(12) United States Patent
Kaplan et al.

(10) Patent No.: US 9,977,026 B2
(45) Date of Patent: May 22, 2018

(54) DETECTION OF ELEVATED LEVELS OF PHOSPHORYLATED MCM AND METHOD OF INCREASING MCM PHOSPHORYLATION CAPACITY

(71) Applicant: The Florida State University Research Foundation, Inc., Tallahassee, FL (US)

(72) Inventors: Daniel L. Kaplan, Tallahassee, FL (US); Irina Bruck, Tallahassee, FL (US)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 140 days.

(21) Appl. No.: 15/221,282

(22) Filed: Jul. 27, 2016

(65) Prior Publication Data
US 2017/0030914 A1    Feb. 2, 2017

Related U.S. Application Data

(60) Provisional application No. 62/199,984, filed on Aug. 1, 2015, provisional application No. 62/324,055, filed on Apr. 18, 2016.

(51) Int. Cl.
*A61K 31/20* (2006.01)
*G01N 33/574* (2006.01)

(52) U.S. Cl.
CPC ... *G01N 33/57419* (2013.01); *G01N 2333/47* (2013.01)

(58) Field of Classification Search
None
See application file for complete search history.

(56) References Cited

U.S. PATENT DOCUMENTS

| | | | |
|---|---|---|---|
| 6,303,323 B1 | 10/2001 | Laskey et al. | |
| 6,711,596 B1 | 3/2004 | Coleman | |
| 7,056,690 B2 | 6/2006 | Laskey et al. | |
| 7,459,157 B2 | 12/2008 | Laskey et al. | |
| 8,148,087 B2 | 4/2012 | Laskey et al. | |
| 8,470,544 B2 | 6/2013 | Laskey et al. | |
| 8,609,351 B2 | 12/2013 | Laskey et al. | |
| 2003/0143646 A1 | 7/2003 | Laskey et al. | |
| 2007/0275421 A1 | 11/2007 | Laskey et al. | |
| 2010/0143943 A1 | 6/2010 | Laskey et al. | |
| 2012/0178103 A1 | 7/2012 | Laskey et al. | |
| 2013/0273577 A1 | 10/2013 | Laskey et al. | |

OTHER PUBLICATIONS

Bonte, D., Lindvall, C., Liu, H., Dykema, K., Furge, K., and Weinreich, M. (2008) Cdc7-Dbf4 kinase overexpression in multiple cancers and tumor cell lines is correlated with p53 inactivation. Neoplasia 10, 920-931.

Davies, R., Miller, R., and Coleman, N. (2005) Colorectal cancer screening: Prospects for molecular stool analysis. Nat Rev Cancer 5, 199-209.

Imperiale, T., Ransohoff, D., Itzkowitz, S., Turnbull, B., and Ross, M. (2004) For the Colorectal Cancer Study Group. Fecal DNAversus fecal occult blood for colorectal-cancer screening in an average-risk population. N Engl J Med 351, 2704-2714.

Jackson, A., Laskey, R., and Coleman, N. (2014) Replication Proteins and Human Disease. Cold Spring Harb Perspect Biol. 6, a013060.

RG, C.-B., R, G.-G., N, M.-F., and R, B.-M. (2015) Immunoexpression of Ki-67, MCM2, and MCM3 in Ameloblastoma and Ameloblastic Carcinoma and Their Correlations with Clinical and Histopathological Patterns. Dis Markers Epub, 683087.

Razavi, S., Jafari, M., Heidarpoor, M., and Khalesi, S. (2015) Minichromosome maintenance-2 (MCM2) expression differentiates oral squamous cell carcinoma from pre-cancerous lesions. Malays J Pathol 37, 253-258.

Joshi, S., Watkins, J., Gazinska, P., Brown, J., Gillett, C., Grigoriadis, A., and Pinder, S. (2015) Digital imaging in the immunohistochemical evaluation of the proliferation markers Ki67, MCM2 and Geminin, in early breast cancer, and their putative prognostic value. BMC Cancer 15, 546.

Zheng, J. (2015) Diagnostic value of MCM2 immunocytochemical staining in cervical lesions and its relationship with HPV infection. Int J Clin Exp Pathol. 8, 875-880.

Hua, C., Zhao, G., Li, Y., and Bie, L. (2014) Minichromosome Maintenance (MCM) Family as potential diagnostic and prognostic tumor markers for human gliomas. BMC Cancer 14, 526.

Stoeber, K., Tlsty, R., Happerfield, L., Thomas, G., Romanov, S., Bobrow, L., Williams, E., and Williams, G. (2001) DNA replication licensing and human cell proliferation. J Cell Sci 114, 2027-2041.

Hiraiwa, A., Fujita, M., Adachi, A., Ono, H., Nagasaka, T., Matsumoto, Y., Ohashi, M., Tomita, Y., and Ishibashi, M. (1998) Specific distribution patterns of hCDC47 expression in cutaneous diseases. J Cutan Pathol 25, 285-290.

Todorov, I., Werness, B., Wang, H., Buddharaju, L., Todorova, P., Slocum, H., Brooks, J., and Huberman, J. (1998) A novel proliferation marker for human tumors and normal tissues. Lab Invest 78, 73-78.

Freeman, A., Morris, L., Mills, A., Stoeber, K., Laskey, R., Williams, G., and Coleman, N. (1999) Minichromosome maintenance proteins as biological markers of dysplasia and malignancy. Clin Cancer Res 5, 2121-2132.

Gonzalez, M., Tachibana, K., Laskey, R., and Coleman, N. (2005) Control of DNA replication and its potential clinical exploitation. Nat Rev Cancer 5, 135-141.

(Continued)

*Primary Examiner* — Changhwa J Cheu
(74) *Attorney, Agent, or Firm* — Nilay J. Choksi; Smith & Hopen, P.A.

(57) ABSTRACT

Identified herein is a novel post-translational modification of Mcm2, wherein the residue of serines 53 and 108 are phosphorylated. DDK phosphorylates Mcm2 at serines 53 and 108 when stimulated by Treslin. DDK is overexpressed in many human cancers, including colorectal cancer, suggesting that monitoring the phosphorylation of Mcm2 at serines 53 and 108 may detect early cancer with high sensitivity and specificity. It was also found that the homologous modification in budding yeast is required for DNA replication, and the modification occurs in cells during active DNA replication only. In an embodiment, the current invention is an antibody specific for human Mcm2 that is phosphorylated at serines 53 and 108. This antibody was found to be overexpressed in colon cancer cell line HCT 116, as well as other cancer cell lines, compared to normal cells.

16 Claims, 14 Drawing Sheets

(56) References Cited

OTHER PUBLICATIONS

Tachibana, K., Gonzalez, M., and Coleman, N. (2005) Cell cycle control of DNA replication and its relevance to cancer pathology. J Pathol 205.
Chatrath, P., Scott, I. S., Morris, L. S., Davies, R. J., Rushbrook, S. M., Bird, K., Vowler, S. L., Grant, J. W., Saeed, I. T., Howard, D., Laskey, R. A., and Coleman, N. (2003) Aberrant expression of minichromosome maintenance protein 2 and Ki67 in laryngeal squamous epithelial lesions. Br. J. Cancer 89, 1048-1054.
Scott, I. S., Morris, L. S., Bird, K., Davies, R. J., Vowler, S. L., Rushbrook, S. M., Marshall, A. E., Laskey, R. A., Miller, R., Arends, M. J., and Coleman, N. (2003) A novel immunohistochemical method to estimate cell-cycle phase distribution in archival tissue: implications fo the prediction outcome in colorectal cancer. J. Pathol. 201, 187-197.
Wharton, S., Chan, K., Anderson, J., Stoeber, K., and Williams, G. (2001) Replicative Mcm2 protein as a novel proliferation marker in oligodendrogliomas and its relationship to Ki67 labelling index, histological grade and prognosis. Neuropathol Appl Neurobiol 27, 305-313.
Dudderidge, T., Stoeber, K., Loddo, M., Atkinson, G., Fanshawe, T., Griffiths, D., and Williams, G. (2005) Mcm2, Geminin, and KI67 define proliferative state and are prognostic markers in renal cell carcinoma. Clin Cancer Res 11, 2510-2517.
Davies, R., Scott, I., Morris, L., Rushbrook, S., Bird, K., Vowler, S., Arends, M., Miller, R., and Coleman, N. (2004) Increased expression of minichromosome maintenance protein 2 in active inflammatory bowel disease. Colorectal Dis Markers 6, 103-110.
Scholzen, T., and Gerdes, J. (2000) The Ki-67 protein: From the known and the unknown. J Cell Physiol 182, 311-322.
Celis, J., and Celis, A. (1985) Cell cycle-dependent variations in the distribution of the nuclear protein cyclin proliferating cell nuclear antigen in cultured cells: Subdivision of S phase. Proc Natl Arad Sci U S A 82, 3262-3266.
Toschi, L., and Bravo, R. (1988) Changes in cyclin/proliferating cell nuclear antigen distribution during DNA repair synthesis. J Cell Biol 107, 1623-1628.
Gonzalez, M., Tachibana, K., Laskey, R., and Coleman, N. (2005) Control of DNA replication and its potential clinical exploitation. Nat Rev Cancer. 5, 135-141.
Gonzalez, M. A., Pinder, S. E., Callagy, G., Vowler, S. L., Morris, L. S., Bird, K., Bell, J. A., Laskey, R. A., and Coleman, N. (2003) Minichromosome maintenance protein 2 is a strong independent prognostic marker in breast cancer. J. Clin. Oncol. 21, 4306-4313.
Meng, M. V., Grossfeld, G. D., Williams, G. H., Dilworth, S., Stoeber, K., Mulley, T. W., Weinberg, V., Carroll, P. R., and Tlsty, T. D. (2001) Minichromosome maintenance protein 2 expression in prostate: characterization and association with outcome after therapy for cancer. Clin Cancer Res 7, 2712-2718.
Rodins, K., Cheale, M., Coleman, N., and Fox, S. (2002) Minichromosome maintenance protein 2 expression in normal kidney and renal cell carcinomas: Relationship to tumor dormancy and potential clinical utility. Clin Cancer Res 8, 1075-1081.
Kruger, S., Thorns, C., Stocker, W., Muller-Kunert, E., Bohle, A., and Feller, A. C. (2003) Prognostic value of MCM2 immunoreactivity in stage T1 transitional cell carcinoma of the bladder. Eur Urol 43, 138-145.
Kato, H., Miyazaki, T., Fuaki, Y., Nakajima, M., Sohda, M., Takita, J., Masuda, N., Fukuchi, M., Manda, R., Ojima, H., Tsukada, K., Asao, T., and Kuwano, H. (2003) A new proliferation marker, minichromosome maintenance protein 2, is associated with tumor aggressiveness in esophageal squamous carcinoma. J. Surg. Oncol. 84, 24-30.
Kodani, I., Osaki, M., Shomori, K., Araki, K., Goto, E., Ryoke, K., and Ito, H. (2003) Minichromosome maintenance 2 expression is correlated with mode of invasion and prognosis in oral squamous cell carcinomas. J Oral Pathol Med. 32, 468-474.
Ramnath, N., Hernandez, F., Tan, D., Huberman, J., Natarajan, N., Beck, A., Hyland, A., Todoro, I., Brooks, J., and Bepler, G. (2001) MCM2 is an independent predictor of survival in patients with non-small-cell lung cancer. J Clin Oncol 19, 4259-4266.
Hashimota, K., Araki, K., Osaki, M., Nakamura, H., Tomita, K., Shimizu, E., and Ito, H. (2004) MCM2 and Ki-67 expression in human lung adenocarcinoma: Prognostic implications. Pathobiology 71, 193-200.
Hunt, D., Freeman, A., Morris, L., Burnet, N., Bird, K., Davies, T., Laskey, R., and Coleman, N. ( 2002) Early recurrence of benign meningioma correlates with expression of mini-chromosome maintenance-2 protein. Br J Neurosurg. 16, 10-15.
Scott, I., Morris, L., Rushbrook, S., Bird, K., Vowler, S., Burne, N., and Coleman, N. (2005) Immunohistochemical estimation of cell cycle entry and phase distribution in astrocytomas: Applications in diagnostic neuropathology. Neuropathol Appl Neurobiol 31, 455-466.
Bruck, I., and Kaplan, D. (2015) The replication initiation protein Sld3/Treslin orchestrates the assembly of the replication fork helicase during S phase. J Biol Chem 290, 27414-27424.
Charych et al., Inhibition of Cdc7/Dbf4 Kinase Activity Affects Specific Phosphorylation Sites on MCM2 in Cancer Cells. Journal of Cellular Biochemistry. 2008. vol. 104: 1075-1086.
Cho et al., CDC7 kinase phosphorlyates serine residues adjacent to acidic amino acids in the minichromosome maintenance 2 protein. PNAS. 2006. vol. 103 (No. 31): 11521-11526.
Kumagai et al., Treslin Collaborates with TopBP1 in Triggering the Initiation of DNA Replication. 2010. Cell. vol. 140 (No. 3): 349-359.
Sansam et al., Cyclin-dependent kinase regulates the length of S phase through TICRR/TRESLIN phosphorylation. Genes & Devlopment. 2015. vol. 29: 555-566.
International Search Report and Written Opinion for PCT/US2016/044289 (filed date: Jul. 27, 2016) dated Oct. 24, 2016; Applicant: The Florida State University Research Foundation, Inc.
Ilves I, Petojevic T, Pesavento J, & Botchan M (2010) Activation of the MCM2-7 Helicase by Association with Cdc45 and GINS Proteins. Mol Cell 37:247-258.
Kamimura Y, Tak YS, Sugino A, & Araki H (2001) Sld3, which interacts with Cdc45 (Sld4), functions for chromosomal DNA replication in *Saccharomyces cerevisiae*. EMBO J 20(8):2097-2107.
Kanemaki M & Labib K (2006) Distinct roles for Sld3 and GINS during establishment and progression of eukaryotic DNA replication forks. EMBO J. 25(8):1753-1763.
Araki H (2010) Cyclin-dependent kinase-dependent initiation of chromosomal DNA replication. Curr Opin Cell Biol 22:766-771.
Labib K (2010) How do Cdc7 and cyclin-dependent kinases trigger the initiation of chromosome replication in eukaryotic cells? Genes Dev. 24:1208-1219.
Remus D, et al. (2009) Concerted loading of Mcm2-7 double hexamers around DNA during DNA replication origin licensing. Cell 139:719-730.
Evrin C, et al. (2009) A double-hexameric MCM2-7 complex is loaded onto origin DNA during licensing of eukaryotic DNA replication. Proc Natl Acad Sci U S A. 106:20240-20245.
Fu, Y., Yardimci, H., Long, D., Ho, T., Guainazzi, A., Bermudez, V., Hurwitz, J., van Oijen, A., Schärer, O., and Walter, J. (2011) Selective bypass of a lagging strand roadblock by the eukaryotic replicative DNA helicase. Cell 146, 931-941.
Zegerman P & Diffley JF (2007) Phosphorylation of Sld2 and Sld3 by cyclin-dependent kinases promotes DNA replication in budding yeast. Nature 445(7125):281-285.
Tanaka S, et al. (2007) CDK-dependent phosphorylation of Sld2 and Sld3 initiates DNA replication in budding yeast. Nature. 445(7125):328-332.
Kumagai A, Shevchenko A, Shevchenko A, & Dunphy W (2011) Direct regulation of Treslin by cyclin-dependent kinase is essential for the onset of DNA replication. J Cell Biol. 193:995-1007.
Tak Y, Tanaka Y, Endo S, Kamimura Y, & Araki H (2006) A CDK-catalysed regulatory phosphorylation for formation of the DNA replication complex Sld2-Dpb11. EMBO J 25:1987-1996.
Kanter D & Kaplan D (2011) Sld2 binds to origin single-stranded DNA and stimulates DNA annealing. Nucleic Acids Res 39:2580-2592.

(56) References Cited

OTHER PUBLICATIONS

Muramatsu S, Hirai K, Tak Y, Kamimura Y, & Araki H (2010) CDK-dependent complex formation between replication proteins Dpb11, Sld2, Pol (epsilon}, and GINS in budding yeast. Genes Dev. 24:602-612.
Dhingra N, Bruck I, Smith S, Ning B, & Kaplan D (2015) Dpb11 helps control assembly of the Cdc45-Mcm2-7-GINS replication fork helicase. J Biol Chem 290:7586-7601.
Bruck I & Kaplan D (2011) Origin Single-stranded DNA Releases Sld3 Protein from the Mcm2-7 Complex, Allowing the GINS Tetramer to Bind the Mcm2-7 Complex. J Biol Chem 286:18602-18613.
Yeeles J, Deegan T, Janska A, Early A, & Diffley J (2015) Regulated eukaryotic DNA replication origin firing with purified proteins. Nature 519:431-435.
Sheu Y & Stillman B (2010) The Dbf4-Cdc7 kinase promotes S phase by alleviating an inhibitory activity in Mcm4. Nature 463:113-117.
Masai H, et al. (2006) Phosphorylation of MCM4 by Cdc7 kinase facilitates its interaction with Cdc45 on the chromatin. J Biol Chem. 281:39249-39261.
Lei M, et al. (1997) MCM2 is a target of regulation by Cdc7-Dbf4 during the initiation of DNA synthesis. Genes Dev 11:3365-3374.
Bruck I & Kaplan DL (2015) The Dbf4-Cdc7 kinase promotes Mcm2-7 ring opening to allow for single-stranded DNA extrusion and helicase assembly. J. Biol Chem. 290:1210-1221.
Bochman M & Schwacha A (2008) The Mcm2-7 complex has in vitro helicase activity. Mol Cell 31:287-293.
Bruck I & Kaplan D (2011) GINS and Sld3 compete with one another for Mcm2-7 and Cdc45 binding. J Biol Chem 286:14157-14167.
Tanaka S, Nakato R, Katou Y, Shirahige K, & Araki H (2011) Origin association of Sld3, Sld7, and Cdc45 proteins is a key step for determination of origin-firing timing. Curr Biol. 21:2055-2063.
Costa A, et al. (2014) DNA binding polarity, dimerization, and ATPase ring remodeling in the CMG helicase of the eukaryotic replisome. Elife Aug. 12:e03273.
Bruck I & Kaplan D (2014) The replication initiation protein sld2 regulates helicase assembly. J Biol Chem 289:1948-1959.
Stead B, Brandl C, & Davey M (2011) Phosphorylation of Mcm2 modulates Mcm2-7 activity and affects the cell's response to DNA damage. Nucleic Acids Res. 39:6998-7008.
Stead B, Brandl C, Sandre M, & Davey M (2012) Mcm2 phosphorylation and the response to replicative stress. BMC Genet 13:36.
Ge X, Jackson D, & Blow J (2007) Dormant origins licensed by excess Mcm2-7 are required for human cells to survive replicative stress. Genes Dev. 21:3331-3341.
Bruck I & Kaplan D (2009) Dbf4-Cdc7 phosphorylation of Mcm2 is required for cell growth. J Biol Chem. 284:28823-28831.
Montagnoli A, et al. (2006) Identification of Mcm2 phosphorylation sites by S-phase-regulating kinases. J Biol Chem 281:10281-10290.
Mantiero D, Mackenzie A, Donaldson A, & Zegerman P (2011) Limiting replication initiation factors execute the temporal programme of origin firing in budding yeast. EMBO J. 30:4805-4814.
Frigola J, Remus D, Mehanna A, & Diffley J (2013) ATPase-dependent quality control of DNA replication origin licensing. Nature 495:339-343.
Samel S, et al. (2014) A unique DNA entry gate serves for regulated loading of the eukaryotic replicative helicase MCM2-7 onto DNA. Genes Dev. 28:1653-1666.
Heller R, et al. (2011) Eukaryotic Origin-Dependent DNA Replication In Vitro Reveals Sequential Action of DDK and S-CDK Kinases. Cell 146:80-91.
Sheu Y, Kinney J, Lengronne A, Pasero P, & Stillman B (2014) Domain within the helicase subunit Mcm4 integrates multiple kinase signals to control DNA replication initiation and fork progression. Proc Natl Acad Sci U S A. 111:E1899-1908.
Sheu Y-J & Stillman B (2006) Cdc7-Dbf4 phosphorylates MCM proteins via a docking site-mediated mechanism to promote S phase progression. Mol Cell 24:101-113.
Francis L, Randell J, Takara T, Uchima L, & Bell S (2009) Incorporation into the prereplicative complex activates the Mcm2-7 helicase for Cdc7-Dbf4 phosphorylation. Genes Dev. 23:643-654.
Yardimci H, Loveland A, Habuchi S, van Oijen A, & Walter J (2010) Uncoupling of Sister Replisomes during Eukaryotic DNA Replication. Mol Cell. 40:834-840.
Simon ME and Schwacha A (2014) The Mcm2-7 Replicative Helicase: A Promising Chemotherapeutic Target. BioMed Research International. vol. 2014, Article ID 549719, 14 pages, 2014.
Sharma SV et al. (2010) Cell line-based platforms to evaluate the therapeutic efficacy of candidate anticancer agents. Nat Rev Cancer. Apr;10(4):241-53.
Wilding JL, and Bodmer WF (2014) Cancer Cell Lines for Drug Discovery and Development. Cancer Res. 74:2377.
Mendez AS et al. (2015) Endoplasmic reticulum stress-independent activation of unfolded protein response kinases by a small molecule ATP-mimic. eLife; 4:e05434.
Niefind K et al. (1999) GTP plus water mimic ATP in the active site of protein kinase CK2, Nature Structural Biology; 6:1100-1103.
Group, U. S. C. S. W. (2015) United States Cancer Statistics: 1999-2012 Incidence and Mortality Web-based Report. Atlanta (GA): Department of Health and Human Services, Centers for Disease Control and Prevention, and National Cancer Institute.
Rhodes, J. (2000) Colorectal cancer screening in the UK: Joint position statement by the British Society of Gastroenterology, the Royal College of Physicians, and the Association of Coloproctology of Great Britain and Ireland. Gut 46, 746-748.
Davies, R., Freeman, A., Morris, L., Bingham, S., Dilworth, S., Scott, I., Laskey, R., Miller, R., and Coleman, N. (2002) Analysis of minichromosome maintenance proteins as a novel method for detection of colorectal cancer in stool. Lancet 359, 1917-1919.
Tognetti S, R. A., Speck C. (2015) Switch on the engine: how the eukaryotic replicative helicase MCM2-7 becomes activated. Chromosoma 124, 13-26.
Forsburg, S. L. (2004) Eukaryotic MCM proteins: beyond replication initiation. Microbiol Mol Biol Rev 68, 109-131.
Bruck, I., and Kaplan, D. (2015) Conserved mechanism for coordinating replication fork helicase assembly with phosphorylation of the helicase. Proc Natl Acad Sci U S A. 112, 11223-11228.

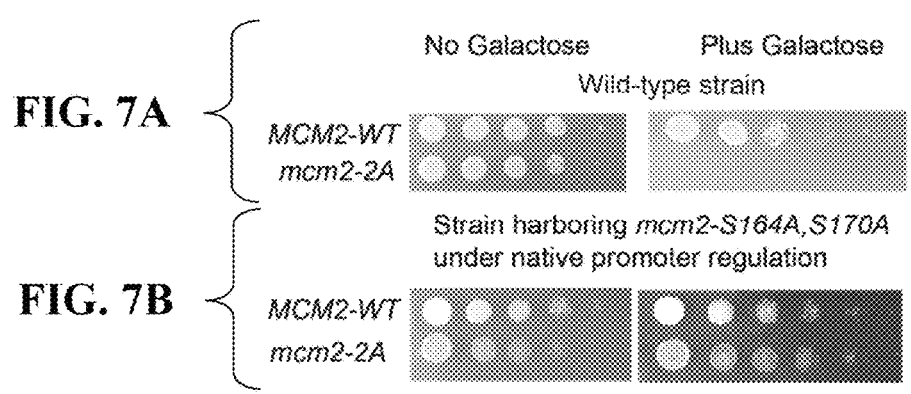

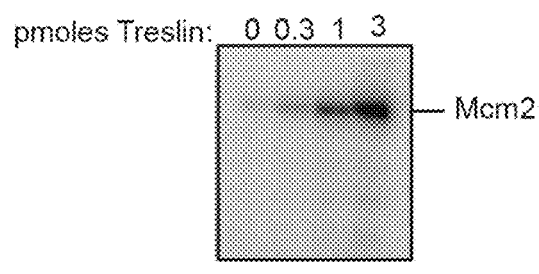
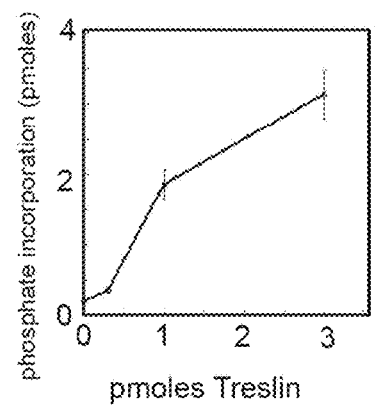
FIG. 12A  FIG. 12B
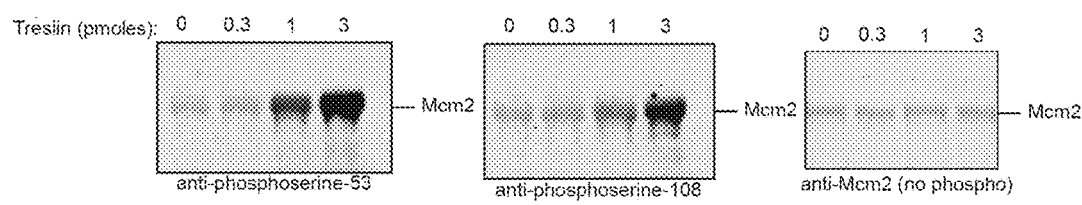
FIG. 12C

SEQUENCE LISTING

```
<160> NUMBER OF SEQ ID NOS: 1

<210> SEQ ID NO 1
<211> LENGTH: 1910
<212> TYPE: PRT
<213> ORGANISM: Homo sapiens

<400> SEQUENCE: 1

Met Ala Cys Cys His Lys Val Met Leu Leu Leu Asp Thr Ala Gly Gly
1               5                   10                  15

Ala Ala Arg His Ser Arg Val Arg Arg Ala Ala Leu Arg Leu Leu Thr
            20                  25                  30

Tyr Leu Ser Cys Arg Phe Gly Leu Ala Arg Val His Trp Ala Phe Lys
        35                  40                  45

Phe Phe Asp Ser Gln Gly Ala Arg Ser Arg Pro Ser Arg Val Ser Asp
```

-continued

```
                 50                  55                  60
Phe Arg Glu Leu Gly Ser Arg Ser Trp Glu Asp Phe Glu Glu Leu
 65                  70                  75                  80
Glu Ala Arg Leu Glu Asp Arg Ala His Leu Pro Gly Pro Ala Pro Arg
                 85                  90                  95
Ala Thr His Thr His Gly Ala Leu Met Glu Thr Leu Leu Asp Tyr Gln
                100                 105                 110
Trp Asp Arg Pro Glu Ile Thr Ser Pro Thr Lys Pro Ile Leu Arg Ser
                115                 120                 125
Ser Gly Arg Arg Leu Leu Asp Val Glu Ser Glu Ala Lys Glu Ala Glu
                130                 135                 140
Ala Ala Leu Gly Gly Leu Val Asn Ala Val Phe Leu Leu Ala Pro Cys
145                 150                 155                 160
Pro His Ser Gln Arg Glu Leu Leu Gln Phe Val Ser Gly Cys Glu Ala
                165                 170                 175
Gln Ala Gln Arg Leu Pro Pro Thr Pro Lys Gln Val Met Glu Lys Leu
                180                 185                 190
Leu Pro Lys Arg Val Arg Glu Val Met Val Ala Arg Lys Ile Thr Phe
                195                 200                 205
Tyr Trp Val Asp Thr Thr Glu Trp Ser Lys Leu Trp Glu Ser Pro Asp
210                 215                 220
His Leu Gly Tyr Trp Thr Val Cys Glu Leu Leu His His Gly Gly Gly
225                 230                 235                 240
Thr Val Leu Pro Ser Glu Ser Phe Ser Trp Asp Phe Ala Gln Ala Gly
                245                 250                 255
Glu Met Leu Leu Arg Ser Gly Ile Lys Leu Ser Ser Glu Pro His Leu
                260                 265                 270
Ser Pro Trp Ile Ser Met Leu Pro Thr Asp Ala Thr Leu Asn Arg Leu
                275                 280                 285
Leu Tyr Asn Ser Pro Glu Tyr Glu Ala Ser Phe Pro Arg Met Glu Gly
                290                 295                 300
Met Leu Phe Leu Pro Val Glu Ala Gly Lys Glu Ile Gln Glu Thr Trp
305                 310                 315                 320
Thr Val Thr Leu Glu Pro Leu Ala Met His Gln Arg His Phe Gln Lys
                325                 330                 335
Pro Val Arg Ile Phe Leu Lys Gly Ser Val Ala Gln Trp Ser Leu Pro
                340                 345                 350
Thr Ser Ser Thr Leu Gly Thr Asp Ser Trp Met Leu Gly Ser Pro Glu
                355                 360                 365
Glu Ser Thr Ala Thr Gln Arg Leu Leu Phe Gln Gln Leu Val Ser Arg
                370                 375                 380
Leu Thr Ala Glu Glu Leu His Leu Val Ala Asp Val Asp Pro Gly Glu
385                 390                 395                 400
Gly Arg Pro Pro Ile Thr Gly Val Ile Ser Pro Leu Ser Ala Ser Ala
                405                 410                 415
Met Ile Leu Thr Val Cys Arg Thr Lys Glu Ala Glu Phe Gln Arg His
                420                 425                 430
Val Leu Gln Thr Ala Val Ala Asp Ser Pro Arg Asp Thr Ala Ser Leu
                435                 440                 445
Phe Ser Asp Val Val Asp Ser Ile Leu Asn Gln Thr His Asp Ser Leu
                450                 455                 460
Ala Asp Thr Ala Ser Ala Ala Ser Pro Val Pro Glu Trp Ala Gln Gln
465                 470                 475                 480
```

```
Glu Leu Gly His Thr Thr Pro Trp Ser Pro Ala Val Glu Lys Trp
            485                 490                 495

Phe Pro Phe Cys Asn Ile Ser Gly Ala Ser Ser Asp Leu Met Glu Ser
            500                 505                 510

Phe Gly Leu Leu Gln Ala Ser Ala Asn Lys Glu Glu Ser Ser Lys
            515                 520                 525

Thr Glu Gly Glu Leu Ile His Cys Leu Ala Glu Leu Tyr Gln Arg Lys
            530                 535                 540

Ser Arg Glu Glu Ser Thr Ile Ala His Gln Glu Asp Ser Lys Lys Lys
545                 550                 555                 560

Arg Gly Val Pro Arg Thr Pro Val Arg Gln Lys Met Asn Thr Met Cys
                565                 570                 575

Arg Ser Leu Lys Met Leu Asn Val Ala Arg Leu Asn Val Lys Ala Gln
            580                 585                 590

Lys Leu His Pro Asp Gly Ser Pro Asp Val Ala Gly Glu Lys Gly Ile
            595                 600                 605

Gln Lys Ile Pro Ser Gly Arg Thr Val Asp Lys Leu Glu Asp Arg Gly
    610                 615                 620

Arg Thr Leu Arg Ser Ser Lys Pro Lys Asp Phe Lys Thr Glu Glu
625                 630                 635                 640

Leu Leu Ser Tyr Ile Arg Glu Asn Tyr Gln Lys Thr Val Ala Thr Gly
                645                 650                 655

Glu Ile Met Leu Tyr Ala Cys Ala Arg Asn Met Ile Ser Thr Val Lys
                660                 665                 670

Met Phe Leu Lys Ser Lys Gly Thr Lys Glu Leu Glu Val Asn Cys Leu
            675                 680                 685

Asn Gln Val Lys Ser Ser Leu Leu Lys Thr Ser Lys Ser Leu Arg Gln
            690                 695                 700

Asn Leu Gly Lys Lys Leu Asp Lys Glu Asp Lys Val Arg Glu Cys Gln
705                 710                 715                 720

Leu Gln Val Phe Leu Arg Leu Glu Met Cys Leu Gln Cys Pro Ser Ile
                725                 730                 735

Asn Glu Ser Thr Asp Asp Met Glu Gln Val Val Glu Glu Val Thr Asp
            740                 745                 750

Leu Leu Arg Met Val Cys Leu Thr Glu Asp Ser Ala Tyr Leu Ala Glu
            755                 760                 765

Phe Leu Glu Glu Ile Leu Arg Leu Tyr Ile Asp Ser Ile Pro Lys Thr
            770                 775                 780

Leu Gly Asn Leu Tyr Asn Ser Leu Gly Phe Val Ile Pro Gln Lys Leu
785                 790                 795                 800

Ala Gly Val Leu Pro Thr Asp Phe Phe Ser Asp Asp Ser Met Thr Gln
                805                 810                 815

Glu Asn Lys Ser Pro Leu Leu Ser Val Pro Phe Leu Ser Ser Ala Arg
            820                 825                 830

Arg Ser Val Ser Gly Ser Pro Glu Ser Asp Glu Leu Gln Glu Leu Arg
            835                 840                 845

Thr Arg Ser Ala Lys Lys Arg Lys Asn Ala Leu Ile Arg His Lys
            850                 855                 860

Ser Ile Ala Glu Val Ser Gln Asn Leu Arg Gln Ile Glu Ile Pro Lys
865                 870                 875                 880

Val Ser Lys Arg Ala Thr Lys Lys Glu Asn Ser His Pro Ala Pro Gln
                885                 890                 895
```

-continued

```
Gln Pro Ser Gln Pro Val Lys Asp Thr Val Gln Glu Val Thr Lys Val
            900                 905                 910

Arg Arg Asn Leu Phe Asn Gln Glu Leu Leu Ser Pro Ser Lys Arg Ser
        915                 920                 925

Leu Lys Arg Gly Leu Pro Arg Ser His Ser Val Ser Ala Val Asp Gly
    930                 935                 940

Leu Glu Asp Lys Leu Asp Asn Phe Lys Lys Asn Lys Gly Tyr His Lys
945                 950                 955                 960

Leu Leu Thr Lys Ser Val Ala Glu Thr Pro Val His Lys Gln Ile Ser
                965                 970                 975

Lys Arg Leu Leu His Arg Gln Ile Lys Gly Arg Ser Ser Asp Pro Gly
            980                 985                 990

Pro Asp Ile Gly Val Val Glu Glu Ser Pro Glu Lys Gly Asp Glu Ile
        995                 1000                1005

Ser Leu Arg Arg Ser Pro Arg Ile Lys Gln Leu Ser Phe Ser Arg
    1010                1015                1020

Thr His Ser Ala Ser Phe Tyr Ser Val Ser Gln Pro Lys Ser Arg
    1025                1030                1035

Ser Val Gln Arg Val His Ser Phe Gln Gln Asp Lys Ser Asp Gln
    1040                1045                1050

Arg Glu Asn Ser Pro Val Gln Ser Ile Arg Ser Pro Lys Ser Leu
    1055                1060                1065

Leu Phe Gly Ala Met Ser Glu Met Ile Ser Pro Ser Glu Lys Gly
    1070                1075                1080

Ser Ala Arg Met Lys Lys Arg Ser Arg Asn Thr Leu Asp Ser Glu
    1085                1090                1095

Val Pro Ala Ala Tyr Gln Thr Pro Lys Lys Ser His Gln Lys Ser
    1100                1105                1110

Leu Ser Phe Ser Lys Thr Thr Pro Arg Arg Ile Ser His Thr Pro
    1115                1120                1125

Gln Thr Pro Leu Tyr Thr Pro Glu Arg Leu Gln Lys Ser Pro Ala
    1130                1135                1140

Lys Met Thr Pro Thr Lys Gln Ala Ala Phe Lys Glu Ser Leu Lys
    1145                1150                1155

Asp Ser Ser Ser Pro Gly His Asp Ser Pro Leu Asp Ser Lys Ile
    1160                1165                1170

Thr Pro Gln Lys Arg His Thr Gln Ala Gly Glu Gly Thr Ser Leu
    1175                1180                1185

Glu Thr Lys Thr Pro Arg Thr Pro Lys Arg Gln Gly Thr Gln Pro
    1190                1195                1200

Pro Gly Phe Leu Pro Asn Cys Thr Trp Pro His Ser Val Asn Ser
    1205                1210                1215

Ser Pro Glu Ser Pro Ser Cys Pro Ala Pro Thr Ser Ser Thr
    1220                1225                1230

Ala Gln Pro Arg Arg Glu Cys Leu Thr Pro Ile Arg Asp Pro Leu
    1235                1240                1245

Arg Thr Pro Pro Arg Ala Ala Ala Phe Met Gly Thr Pro Gln Asn
    1250                1255                1260

Gln Thr His Gln Gln Pro His Val Leu Arg Ala Ala Arg Ala Glu
    1265                1270                1275

Glu Pro Ala Gln Lys Leu Lys Asp Lys Ala Ile Lys Thr Pro Lys
    1280                1285                1290

Arg Pro Gly Asn Ser Thr Val Thr Ser Ser Pro Pro Val Thr Pro
```

```
            1295                1300                1305
Lys Lys Leu Phe Thr Ser Pro Leu Cys Asp Val Ser Lys Lys Ser
    1310                1315                1320
Pro Phe Arg Lys Ser Lys Ile Glu Cys Pro Ser Pro Gly Glu Leu
    1325                1330                1335
Asp Gln Lys Glu Pro Gln Met Ser Pro Ser Val Ala Ala Ser Leu
    1340                1345                1350
Ser Cys Pro Val Pro Ser Thr Pro Pro Glu Leu Ser Gln Arg Ala
    1355                1360                1365
Thr Leu Asp Thr Val Pro Pro Pro Pro Ser Lys Val Gly Lys
    1370                1375                1380
Arg Cys Arg Lys Thr Ser Asp Pro Arg Arg Ser Ile Val Glu Cys
    1385                1390                1395
Gln Pro Asp Ala Ser Ala Thr Pro Gly Val Gly Thr Ala Asp Ser
    1400                1405                1410
Pro Ala Ala Pro Thr Asp Ser Arg Asp Asp Gln Lys Gly Leu Ser
    1415                1420                1425
Leu Ser Pro Gln Ser Pro Pro Glu Arg Arg Gly Tyr Pro Gly Pro
    1430                1435                1440
Gly Leu Arg Ser Asp Trp His Ala Ser Ser Pro Leu Leu Ile Thr
    1445                1450                1455
Ser Asp Thr Glu His Val Thr Leu Leu Ser Glu Ala Glu His His
    1460                1465                1470
Gly Ile Gly Asp Leu Lys Ser Asn Val Leu Ser Val Glu Glu Gly
    1475                1480                1485
Glu Gly Leu Arg Thr Ala Asp Ala Glu Lys Ser Ser Leu Ser His
    1490                1495                1500
Pro Gly Ile Pro Pro Ser Pro Pro Ser Cys Gly Pro Gly Ser Pro
    1505                1510                1515
Leu Met Pro Ser Arg Asp Val His Cys Thr Thr Asp Gly Arg Gln
    1520                1525                1530
Cys Gln Ala Ser Ala Gln Leu Asp Asn Leu Pro Ala Ser Ala Trp
    1535                1540                1545
His Ser Thr Asp Ser Ala Ser Pro Gln Thr Tyr Glu Val Glu Leu
    1550                1555                1560
Glu Met Gln Ala Ser Gly Leu Pro Lys Leu Arg Ile Lys Lys Ile
    1565                1570                1575
Asp Pro Ser Ser Ser Leu Glu Ala Glu Pro Leu Ser Lys Glu Glu
    1580                1585                1590
Ser Ser Leu Gly Glu Glu Ser Phe Leu Pro Ala Leu Ser Met Pro
    1595                1600                1605
Arg Ala Ser Arg Ser Leu Ser Lys Pro Glu Pro Thr Tyr Val Ser
    1610                1615                1620
Pro Pro Cys Pro Arg Leu Ser His Ser Thr Pro Gly Lys Ser Arg
    1625                1630                1635
Gly Gln Thr Tyr Ile Cys Gln Ala Cys Thr Pro Thr His Gly Pro
    1640                1645                1650
Ser Ser Thr Pro Ser Pro Phe Gln Thr Asp Gly Val Pro Trp Thr
    1655                1660                1665
Pro Ser Pro Lys His Ser Gly Lys Thr Thr Pro Asp Ile Ile Lys
    1670                1675                1680
Asp Trp Pro Arg Arg Lys Arg Ala Val Gly Cys Gly Ala Gly Ser
    1685                1690                1695
```

-continued

```
Ser Ser Gly Arg Gly Glu Val Gly Ala Asp Leu Pro Gly Ser Leu
    1700                1705            1710

Ser Leu Leu Glu Ser Glu Gly Lys Asp His Gly Leu Glu Leu Ser
    1715                1720            1725

Ile His Arg Thr Pro Ile Leu Glu Asp Phe Glu Leu Glu Gly Val
    1730                1735            1740

Cys Gln Leu Pro Asp Gln Ser Pro Pro Arg Asn Ser Met Pro Lys
    1745                1750            1755

Ala Glu Glu Ala Ser Ser Trp Gly Gln Phe Gly Leu Ser Ser Arg
    1760                1765            1770

Lys Arg Val Leu Leu Ala Lys Glu Glu Ala Asp Arg Gly Ala Lys
    1775                1780            1785

Arg Ile Cys Asp Leu Arg Glu Asp Ser Glu Val Ser Lys Ser Lys
    1790                1795            1800

Glu Gly Ser Pro Ser Trp Ser Ala Trp Gln Leu Pro Ser Thr Gly
    1805                1810            1815

Asp Glu Glu Val Phe Val Ser Gly Ser Thr Pro Pro Pro Ser Cys
    1820                1825            1830

Ala Val Arg Ser Cys Leu Ser Ala Ser Ala Leu Gln Ala Leu Thr
    1835                1840            1845

Gln Ser Pro Leu Leu Phe Gln Gly Lys Thr Pro Ser Ser Gln Ser
    1850                1855            1860

Lys Asp Pro Arg Asp Glu Asp Val Asp Val Leu Pro Ser Thr Val
    1865                1870            1875

Glu Asp Ser Pro Phe Ser Arg Ala Phe Ser Arg Arg Arg Pro Ile
    1880                1885            1890

Ser Arg Thr Tyr Thr Arg Lys Lys Leu Met Gly Thr Trp Leu Glu
    1895                1900            1905

Asp Leu
    1910
```

US 9,977,026 B2

DETECTION OF ELEVATED LEVELS OF PHOSPHORYLATED MCM AND METHOD OF INCREASING MCM PHOSPHORYLATION CAPACITY

CROSS-REFERENCE TO RELATED APPLICATIONS

This nonprovisional application claims priority to U.S. Provisional Patent Application No. 62/199,984, entitled "Screening Assay for DDK Modulators", filed Aug. 1, 2015, and to U.S. Provisional Patent Application No. 62/324,055, entitled "Antibody-Based Screening Assay for Cancers and Other Diseases of Cell Proliferation", filed Apr. 18, 2016, both of which are incorporated herein by reference in their entireties.

FEDERALLY SPONSORED RESEARCH OR DEVELOPMENT

This invention was made with Government support under Grant No. 1265431 awarded by the National Science Foundation. The government has certain rights in the invention.

BACKGROUND OF THE INVENTION

1. Field of the Invention

This invention relates, generally, to screening assays for diseases and disorders related to cell proliferation. More particularly, it relates to specific antibody-based screening assays for colorectal cancer.

2. Brief Description of the Prior Art

Many common cancers can be treated more successfully when they are detected early, either as precursor lesions or early-stage malignancies, though the choice of markers for early detection is a challenge. The aim is to distinguish normal cells from cancer cells, irrespective of the oncogenes or tumor-suppressor genes that the cancer cells mis-express. Abundant evidence indicates that DNA replication proteins are exceptionally good markers for early detection of many of the common carcinomas and that they can also provide clinically useful prognostic information. The Mcm2 protein is particularly valuable in this role, outperforming both PCNA and Ki67, which are two other replication proteins that have also been used for this purpose (Davies, R., Miller, R., and Coleman, N. (2005) Colorectal cancer screening: Prospects for molecular stool analysis. Nat Rev Cancer 5, 199-209; RG, C.-B., R, G.-G., N, M.-F., and R, B.-M. (2015) Immunoexpression of Ki-67, MCM2, and MCM3 in Ameloblastoma and Ameloblastic Carcinoma and Their Correlations with Clinical and Histopathological Patterns. *Dis Markers* Epub, 683087; Razavi, S., Jafari, M., Heidarpoor, M., and Khalesi, S. (2015) Minichromosome maintenance-2 (MCM2) expression differentiates oral squamous cell carcinoma from pre-cancerous lesions. *Malays J Pathol* 37, 253-258; Joshi, S., Watkins, J., Gazinska, P., Brown, J., Gillett, C., Grigoriadis, A., and Pinder, S. (2015) Digital imaging in the immunohistochemical evaluation of the proliferation markers Ki67, MCM2 and Geminin, in early breast cancer, and their putative prognostic value. *BMC Cancer* 15, 546; Zheng, J. (2015) Diagnostic value of MCM2 immunocytochemical staining in cervical lesions and its relationship with HPV infection. *Int J Clin Exp Pathol.* 8, 875-880; Hua, C., Zhao, G., Li, Y., and Bie, L. (2014) Minichromosome Maintenance (MCM) Family as potential diagnostic and prognostic tumor markers for human gliomas. *BMC Cancer* 14, 526).

Dysregulation of DNA replication is fundamental for uncontrolled cellular proliferation, and the clinical targeting of eukaryotic replication factors has seen widespread use in cancer treatment paradigms. Small molecule inhibitors that target leading or lagging strand synthesis, such as topoisomerases, DNA polymerases, DNA ligase, proliferating cell nuclear antigen (PCNA), ribonucleotide reductase, and telomerase, have been developed to clinically block uncontrolled cancer proliferation (Simon M E and Schwacha A (2014) The Mcm2-7 Replicative Helicase: A Promising Chemotherapeutic Target. BioMed Research International. vol. 2014, Article ID 549719, 14 pages, 2014). Although these compounds have demonstrated utility as chemotherapeutic agents, they are non-specific in that they target both normal and malignant DNA replication and, therefore, exhibit side effects. Unfortunately, few inhibitors that target replication initiation have been identified.

The essential role of Mcm2 in proliferation explains why Mcm2 is a useful biomarker for early detection of cancer by screening (Davies, R., Miller, R., and Coleman, N. (2005) Colorectal cancer screening: Prospects for molecular stool analysis. *Nat Rev Cancer* 5, 199-209). Mcm2 is expressed through all phases of the cell cycle but is lost when cells exit the cycle into quiescence, senescence, or differentiation (Stoeber, K., Tlsty, R., Happerfield, L., Thomas, G., Romanov, S., Bobrow, L., Williams, E., and Williams, G. (2001) DNA replication licensing and human cell proliferation. *J Cell Sci* 114, 2027-2041). Although Mcm2 binds to and detaches from DNA according to cell cycle phase, Mcm2 remains in the nucleus of higher eukaryotes throughout the cell cycle. In malignant and premalignant lesions of differentiating epithelia, there is a substantial increase in the number of cells expressing Mcm2 (Hiraiwa, A., Fujita, M., Adachi, A., Ono, H., Nagasaka, T., Matsumoto, Y., Ohashi, M., Tomita, Y., and Ishibashi, M. (1998) Specific distribution patterns of hCDC47 expression in cutaneous diseases. *J Cutan Pathol* 25, 285-290; Todorov, I., Werness, B., Wang, H., Buddharaju, L., Todorova, P., Slocum, H., Brooks, J., and Huberman, J. (1998) A novel proliferation marker for human tumors and normal tissues. *Lab Invest* 78, 73-78; Freeman, A., Morris, L., Mills, A., Stoeber, K., Laskey, R., Williams, G., and Coleman, N. (1999) Minichromosome maintenance proteins as biological markers of dysplasia and malignancy. *Clin Cancer Res* 5, 2121-2132). One of the characteristic features of dysplastic and malignant cells may be that they express Mcm2 (21,22).

The sensitivity of an Mcm2-based test is superior to those using other currently used markers of cell cycle entry, such as Ki67 and PCNA. Fewer cells express Ki67 than Mcm2 in malignant and dysplastic lesions. Ki67 is not expressed by all cycling cells, including cells in S phase. Furthermore, the function of Ki67 in the cell cycle remains poorly understood. PCNA shows wide variation in staining intensity in vivo. This is consistent with fluctuations in expression levels of PCNA during the cell cycle. Moreover, important roles for PCNA in DNA repair mean that PCNA is still present in non-proliferating cells and therefore less useful as a specific marker of cancer. Testing for Mcm2 represents a proven method for detecting expression of a protein at the point where growth-signaling pathways converge in the initiation of DNA replication (Gonzalez, M., Tachibana, K., Laskey, R., and Coleman, N. (2005) Control of DNA replication and its potential clinical exploitation. *Nat Rev Cancer.* 5, 135-141). Far less literature is available regarding the potential translational value of other replication proteins.

Approximately 4.5% of men and women will be diagnosed with colon and rectal cancer at some point in their lifetime. In 2012, there were an estimated 1,168,929 people living with colon and rectum cancer in the United States. For colon and rectum cancer, 39.5% are diagnosed at the local stage. The earlier that colon and rectal cancer is caught, the better the person has of surviving five (5) years after being diagnosed. The 5-year survival for localized colon and rectum cancer is 90.1%. It is thought to take two to three years for an asymptomatic early colorectal cancer to develop into a symptomatic advanced lesion.

There is a pressing need for new screening tests based on the increasing understanding of the biology and natural history of colorectal cancer. An effective strategy for early detection of colorectal cancer would produce very substantial benefits in overall survival. Current screening tests either detect the presence of occult blood in stool or identify gross abnormalities by endoscopy (Imperiale, T., Ransohoff, D., Itzkowitz, S., Turnbull, B., and Ross, M. (2004) For the Colorectal Cancer Study Group. Fecal DNA versus fecal occult blood for colorectal-cancer screening in an average-risk population. *N Engl J Med* 351, 2704-2714). Stool testing is likely to be particularly valuable, as it represents a non-invasive method for screening all of the colon and rectum without the need for bowel preparation. Methods for retrieving colon cells from stool washings are now available (Davies, R., Freeman, A., Morris, L., Bingham, S., Dilworth, S., Scott, I., Laskey, R., Miller, R., and Coleman, N. (2002) Analysis of minichromosome maintenance proteins as a novel method for detection of colorectal cancer in stool. *Lancet* 359, 1917-1919). However, all current tests are limited in their effectiveness and/or patient acceptability (Jackson, A., Laskey, R., and Coleman, N. (2014) Replication Proteins and Human Disease. *Cold Spring Harb Perspect Biol.* 6, a013060).

The replication fork helicase in eukaryotes is composed of Cdc45, the Mcm2-7 heterohexameric ATPase, and the tetrameric GINS complex (CMG assembly). The replication fork helicase (CMG) assembles in S phase in a manner that is dependent upon the replication initiation factors Sld2, Sld3, and Dpb11. Sld3 (Treslin/TICRR in humans), Sld2 (RecQL4/RecQ4 in humans), and Dpb11 (TopBP1 in humans) are required for the initiation of DNA replication, but these proteins do not travel with the replication fork. The S-phase specific kinases, cyclin-dependent kinase (CDK) and the Dbf4-dependent kinase (DDK), are also required for CMG assembly and origin activation. In late M and $G_1$ phases, the Mcm2-7 complex loads to encircle double-stranded DNA (dsDNA) as a double hexamer. During S phase, a single-strand of DNA is extruded from the central channel of Mcm2-7, and this event is required since the CMG complex unwinds DNA by a steric exclusion mechanism.

Central to the initiation of DNA replication is the coordination of entry into S phase with origin firing. Levels of the S phase-specific kinases, S-CDK and DDK, rise during the onset of S phase, and these two kinases are central to coordinating S phase entry with origin firing. S-CDK phosphorylates Sld2 and Sld3, and these phosphorylation events are the essential functions of S-CDK (9, 10). S-CDK phosphorylation of Sld3 is conserved in human Treslin (Kumagai A, Shevchenko A, Shevchenko A, & Dunphy W (2011) Direct regulation of Treslin by cyclin-dependent kinase is essential for the onset of DNA replication. J Cell Biol. 193:995-1007). S-CDK phosphorylation of Sld2 promotes the association of Sld2 with yeast Dpb11 (Tak Y, Tanaka Y, Endo S, Kamimura Y, & Araki H (2006) A CDK-catalysed regulatory phosphorylation for formation of the DNA replication complex Sld2-Dpb11. EMBO J 25:1987-1996), and also the association of Sld2 with T-rich ssDNA (Kanter D & Kaplan D (2011) Sld2 binds to origin single-stranded DNA and stimulates DNA annealing. Nucleic Acids Res 39:2580-2592). S-CDK phosphorylation of Sld3 stimulates the association of Sld3 with Dpb11. The associations of Sld2 with Dpb11 and Sld3 with Dpb11 have been proposed to be important for the recruitment of GINS to origins, through the generation of a pre-loading complex (Pre-LC), composed of Sld2, GINS, Polε, and Dpb11 (14). S-CDK-catalyzed formation of an Sld3-Dpb11-Sld2 complex has also been proposed to be important to generate a ternary ssDNA-binding complex of high affinity, since Sld2, Sld3, and Dpb11 bind to T-rich ssDNA.

The essential role of DDK in yeast cells is the phosphorylation of subunits of the Mcm2-7 complex (Yeeles J, Deegan T, Janska A, Early A, & Diffley J (2015) Regulated eukaryotic DNA replication origin firing with purified proteins. Nature 519:431-435). DDK phosphorylation of Mcm4 is important for cell growth, and this phosphorylation event alleviates an inhibitory function of the N-terminus of Mcm4. DDK phosphorylation of Mcm4 may also promote the interaction between Cdc45 and Mcm2-7 (Sheu Y & Stillman B (2010) The Dbf4-Cdc7 kinase promotes S phase by alleviating an inhibitory activity in Mcm4. Nature 463:113-117). DDK phosphorylation of Mcm6 may also be important for cell growth (Masai H, et al. (2006) Phosphorylation of MCM4 by Cdc7 kinase facilitates its interaction with Cdc45 on the chromatin. J Biol Chem. 281:39249-39261). Mcm2 is also a target for DDK (Lei M, et al. (1997) MCM2 is a target of regulation by Cdc7-Dbf4 during the initiation of DNA synthesis. Genes Dev 11:3365-3374), and DDK phosphorylation of Mcm2 is also required for DNA replication under normal growth conditions (Bruck I & Kaplan D L (2015) The Dbf4-Cdc7 kinase promotes Mcm2-7 ring opening to allow for single-stranded DNA extrusion and helicase assembly. J. Biol Chem. 290:1210-1221). Furthermore, expression of a mutant of mcm2 (mcm2-S164A,S170A) that is not phosphorylated by DDK exerts a dominant-negative severe growth defect in budding yeast that is bypassed by the mcm5-bob1 (mcm5-P83L) mutation. The biochemical mechanism of this genetic suppression has also been examined. DDK phosphorylation of Mcm2 reduces the affinity of budding yeast Mcm2 for Mcm5, and the mcm5-bob1 mutation also reduces this affinity. This reduced affinity may help open the 'Mcm2-Mcm5 gate,' which may be important for the extrusion of ssDNA from the central channel of Mcm2-7 during S phase, a requirement for origin activation.

Cdc45 binds weakly to Mcm2-7 in the absence of accessory factors (Bruck I & Kaplan D (2011) GINS and Sld3 compete with one another for Mcm2-7 and Cdc45 binding. J Biol Chem 286:14157-14167). Sld3 binds tightly to Mcm2-7 and Cdc45, and thus Sld3 recruits Cdc45 to Mcm2-7 complexes. This step may further require DDK and involve the nonessential initiation factor Sld7. During origin activation, Sld3 is removed from Mcm2-7, presumably through the exposure of sequestering T-rich ssDNA. GINS can substitute for Sld3 as a factor that promotes the association of Cdc45 with Mcm2-7, thereby forming the stable Cdc45-Mcm2-7-GINS (CMG) replicative helicase complex.

The mechanism of GINS recruitment may involve the formation of the S-CDK-dependent pre-loading complex, wherein the pre-LC recruits GINS to Mcm2-7, analogous to how Sld3 recruits Cdc45 to Mcm2-7 (14). A second proposal posits that Sld3, Sld2, and Dpb11 compete with GINS for binding to Mcm2-7 prior to origin activation, blocking the premature interaction between GINS and Mcm2-7 prior to origin activation. However, when T-rich ssDNA is extruded from the central channel of Mcm2-7, an ssDNA binding surface for Sld3-Sld2-Dpb11 is generated. Sld3-Sld2-Dpb11 dissociates from Mcm2-7 once the origin is melted, since Sld3-Sld2-Dpb11 has a higher affinity for ssDNA then Mcm2-7. The dissociation of Sld3-Sld2-Dpb11 from Mcm2-7 allows GINS to bind Mcm2-7 by a passive, sequestration mechanism. The two models are not incompatible with one another, and they may both be correct.

There is an excess of Mcm2-7 double hexamer complexes loaded onto dsDNA in M phase and $G_1$ relative to the number of Mcm2-7 double hexamer complexes that actually fire. Remarkably, the activated Mcm2-7 complexes share several features in common: DDK phosphorylation of Mcm2-7, initiation factor (Sld3, Sld2, Dpb11, Mcm10, and Sld7) binding to Mcm2-7, and Cdc45/GINS attachment to Mcm2-7. However, it is unknown what coordinates these different activities at a particular Mcm2-7 double hexamer. In other words, the mechanism that prevents Cdc45 from binding to one Mcm2-7 double hexamer, while DDK phosphorylates a different Mcm2-7 double hexamer, is unknown.

The Mcm2 protein, in particular, a component of the DNA replication apparatus, is currently being developed for its use as an early marker of colorectal cancer in cells from stool washings. Mcm2 is a subunit of the replication fork helicase, the macromolecular assembly that unwinds DNA at a replication fork.

In an initial clinical evaluation study, Mcm2-positive cells were retrieved from the stool of 37 of 40 patients with colorectal cancer, including all nine early-stage cancers, but from none of 25 control participants (Davies, R., Freeman, A., Morris, L., Bingham, S., Dilworth, S., Scott, I., Laskey, R., Miller, R., and Coleman, N. (2002) Analysis of minichromosome maintenance proteins as a novel method for detection of colorectal cancer in stool. *Lancet* 359, 1917-1919). Furthermore, immunohistochemistry for cell cycle proteins can address a further important challenge in diagnostic pathology, predicting the outcome of tumors using tissue sections of clinical samples. Markers that can be detected in routinely processed sections of formalin-fixed, paraffin-embedded tissue are particularly valuable. For many tumors, powerful prognostic information is provided by quantitative assessment of cell cycle entry and/or particular cell cycle phases. As accurate indicators of cell cycle state, Mcm2 has been shown to predict survival in patients with a range of tumors, including malignancies of breast (Gonzalez, M. A., Pinder, S. E., Callagy, G., Vowler, S. L., Morris, L. S., Bird, K., Bell, J. A., Laskey, R. A., and Coleman, N. (2003) Minichromosome maintenance protein 2 is a strong independent prognostic marker in breast cancer. *J. Clin. Oncol.* 21, 4306-4313), prostate (Meng, M. V., Grossfeld, G. D., Williams, G. H., Dilworth, S., Stoeber, K., Mulley, T. W., Weinberg, V., Carroll, P. R., and Tlsty, T. D. (2001) Minichromosome maintenance protein 2 expression in prostate: characterization and association with outcome after therapy for cancer. *Clin Cancer Res* 7, 2712-2718), kidney (Rodins, K., Cheale, M., Coleman, N., and Fox, S. (2002) Minichromosome maintenance protein 2 expression in normal kidney and renal cell carcinomas: Relationship to tumor dormancy and potential clinical utility. *Clin Cancer Res* 8, 1075-1081), bladder (Kruger, S., Thorns, C., Stocker, W., Muller-Kunert, E., Bohle, A., and Feller, A. C. (2003) Prognostic value of MCM2 immunoreactivity in stage Ti transitional cell carcinoma of the bladder. *Eur Urol* 43, 138-145), esophagus (Kato, H., Miyazaki, T., Fuaki, Y., Nakajima, M., Sohda, M., Takita, J., Masuda, N., Fukuchi, M., Manda, R., Ojima, H., Tsukada, K., Asao, T., and Kuwano, H. (2003) A new proliferation marker, minichromosome maintenance protein 2, is associated with tumor aggressiveness in esophogeal squamous carcinoma. *J. Surg. Oncol.* 84, 24-30), mouth (Kodani, I., Osaki, M., Shomori, K., Araki, K., Goto, E., Ryoke, K., and Ito, H. (2003) Minichromosome maintenance 2 expression is correlated with mode of invasion and prognosis in oral squamous cell carcinomas. *J Oral Pathol Med.* 32, 468-474), lung (Ramnath, N., Hernandez, F., Tan, D., Huberman, J., Natarajan, N., Beck, A., Hyland, A., Todoro, I., Brooks, J., and Bepler, G. (2001) MCM2 is an independent predictor of survival in patients with non-small-cell lung cancer. *J Clin Oncol* 19, 4259-4266; Hashimoto, K., Araki, K., Osaki, M., Nakamura, H., Tomita, K., Shimizu, E., and Ito, H. (2004) MCM2 and Ki-67 expression in human lung adenocarcinoma: Prognostic implications. *Pathobiology* 71, 193-200) and brain (harton, S., Chan, K., Anderson, J Stoeber, K., and Williams, G. (2001) Replicative Mcm2 protein as a novel proliferation marker in oligodendrogliomas and its relationship to Ki67 labelling index, histological grade and prognosis. *Neuropathol Appl Neurobiol* 27, 305-313; Hunt, D., Freeman, A., Morris, L., Burnet, N., Bird, K., Davies, T., Laskey, R., and Coleman, N. (2002) Early recurrence of benign meningioma correlates with expression of mini-chromosome maintenance-2 protein. *Br J Neurosurg.* 16, 10-15; Scott, I., Morris, L., Rushbrook, S., Bird, K., Vowler, S., Burne, N., and Coleman, N. (2005) Immunohistochemical estimation of cell cycle entry and phase distribution in astrocytomas: Applications in diagnostic neuropathology. *Neuropathol Appl Neurobiol* 31, 455-466). Moreover, for the data sets analyzed, the Mcm2 labeling index was also superior to clinico-pathological parameters that are currently widely used to predict outcome, namely, histological grade and lymph node stage. Furthermore, DDK, which phosphorylates Mcm2 at serine 53, is overexpressed in colorectal cancer cells (Bonte, D., Lindvall, C., Liu, H., Dykema, K., Furge, K., and Weinreich, M. (2008) Cdc7-Dbf4 kinase overexpression in multiple cancers and tumor cell lines is correlated with p53 inactivation. *Neoplasia* 10, 920-931).

It was found that in budding yeast, a model organism for DNA replication, Mcm2 is phosphorylated by DDK in a manner that is stimulated by the replication initiation protein Sld3 (Bruck, I., and Kaplan, D. (2015) The replication initiation protein Sld3/Treslin orchestrates the assembly of the replication fork helicase during S phase. *J Biol Chem* 290, 27414-27424). DDK phosphorylates serine 170 of Mcm2, and this single phosphorylation event is essential for the initiation of DNA replication (Hua, C., Zhao, G., Li, Y., and Bie, L. (2014) Minichromosome Maintenance (MCM) Family as potential diagnostic and prognostic tumor markers for human gliomas. *BMC Cancer* 14, 526; Toschi, L., and Bravo, R. (1988) Changes in cyclin/proliferating cell nuclear antigen distribution during DNA repair synthesis. *J Cell Biol* 107, 1623-1628). DDK phosphorylation of Mcm2 is essential because this phosphorylation event opens the helicase ring, allowing single-stranded DNA to be melted at an origin of replication (Hua, C., Zhao, G., Li, Y., and Bie, L. (2014) Minichromosome Maintenance (MCM) Family as potential diagnostic and prognostic tumor markers for human gliomas. *BMC Cancer* 14, 526). Melting of origin DNA is essential because it allows for the genomic DNA to be subsequently unwound by the helicase during DNA replication (Hua, C., Zhao, G., Li, Y., and Bie, L. (2014) Minichromosome Maintenance (MCM) Family as potential diagnostic and prognostic tumor markers for human gliomas. *BMC Cancer* 14, 526).

It was also found that in human cells, the analogous phosphorylation reaction occurs, and DDK phosphorylates human Mcm2 at serine 53 (Bruck, I., and Kaplan, D. (2015) The replication initiation protein Sld3/Treslin orchestrates the assembly of the replication fork helicase during S phase. *J Biol Chem* 290, 27414-27424). The human homolog of Sld3, called Treslin, stimulates this phosphorylation event (Id.). Thus, DDK phosphorylation of Mcm2 is a fundamental event in the cell cycle that triggers the initiation of DNA replication (Id.). This reaction is conserved from yeast to humans (Id.). For these reasons, probing for DDK-phosphorylated Mcm2, instead of the traditional Mcm2, is potentially a more specific assay for detecting early cancer. Whereas the current tumor marker Mcm2 is present at equal levels throughout the cell cycle, phosphorylated Mcm2 is present at substantially higher levels during S phase, when DNA replication is active (Hua, C., Zhao, G., Li, Y., and Bie, L. (2014) Minichromosome Maintenance (MCM) Family as potential diagnostic and prognostic tumor markers for human gliomas. *BMC Cancer* 14, 526). Since cancer cells spend a higher fraction of time in S phase compared to normal cells, cancer cells will likely have higher levels of DDK-phosphorylated-Mcm2 compared to normal cells (Davies, R., Miller, R., and Coleman, N. (2005) Colorectal cancer screening: Prospects for molecular stool analysis. *Nat Rev Cancer* 5, 199-209). In addition, colorectal cancer cells have higher levels of DDK than normal cells, suggesting that Mcm2-S53P will be abundant in colorectal cancer cells (Bonte, D., Lindvall, C., Liu, H., Dykema, K., Furge, K., and Weinreich, M. (2008) Cdc7-Dbf4 kinase overexpression in multiple cancers and tumor cell lines is correlated with p53 inactivation. *Neoplasia* 10, 920-931).

The sensitivity of an Mcm2-based test is superior to those using conventional markers of cell cycle entry, such as Ki67 and PCNA. Ki67 is not expressed by all cycling cells, including cells in S phase. Moreover, important roles for PCNA in DNA repair mean that PCNA is still present in non-proliferating cells and therefore less useful as a specific marker of cancer. Testing for Mcm2 is a proven method for detecting expression of a DNA replication protein. However, Mcm2 lacks specificity, because it is present in all stages of the cell cycle.

Accordingly, what is needed is a more directed, effective screening assay based on an antibody specific for a phosphorylated Mcm2. However, in view of the art considered as a whole at the time the present invention was made, it was not obvious to those of ordinary skill in the field of this invention how the shortcomings of the prior art could be overcome.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for an improved assay for detection of phosphorylated Mcm and early diagnosis of cancer is now met by a new, useful, and nonobvious invention.

In an embodiment, the current invention is a method of detecting elevated levels of phosphorylated Mcm (e.g., Mcm2, for example at serines 53 and/or 108) in a patient. A sample (e.g., tissue sample) is obtained from a human patient, and in that sample, an elevated level of phosphorylated Mcm can be detected (relative to normal levels) by contacting the sample with an anti-Mcm antibody and detecting binding between the phosphorylated Mcm and the antibody.

In a separate embodiment, the current invention is a method of diagnosing cancer (e.g., colon cancer and/or rectal cancer) in a patient. A sample is obtained from a human patient, and in that sample, an elevated level of phosphorylated Mcm can be detected (relative to normal levels) by contacting the sample with an anti-Mcm antibody and detecting binding between the phosphorylated Mcm and the antibody. The patient can then be diagnosed with cancer when an elevated level of phosphorylated Mcm is detected.

In yet another embodiment, the current invention is a method of increasing capacity for phosphorylation of Mcm (e.g., Mcm2 is at serine 53 or serine 108) in a biological sample. Specifically, Mcm's capacity for phosphorylation is increased by administering a clinically effective amount (e.g., 3 pmoles) of purified Treslin to increase phosphorylation of Mcm by DDK, whereby DDK is recruited to Mcm to bridge DDK and Mcm together in an active state.

One of a plurality of phosphorylation-stimulating fragments thereof can be used to stimulate this phosphorylation; these fragments are amino acids 833-1133, amino acids 833-1267, amino acids 833-1910, amino acids 833-1000, amino acids 1000-1267, and amino acids 1000-1133 of SEQ ID NO:1.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which:

FIGS. 1A-1E show that Sld3 substantially stimulates DDK phosphorylation of Mcm2.

FIGS. 2A-2D show that Sld3 stimulation of DDK phosphorylation of Mcm2 is required for cell growth and DNA replication.

FIGS. 3A-3B show that Sld3 stimulation of DDK phosphorylation of Mcm2 is required for GINS association with Mcm2-7 during S phase.

FIG. 7A depicts a consequence of overexpression of mcm2-2A (mcm2-S164A,S170A) in normal, wild-type budding yeast (21).

FIG. 7B depicts a consequence of overexpression of mcm2-2A (mcm2-S164A,S170A) in the strain harboring mcm2-S160AS170A (28).

FIGS. 8A-8E show that sld3-m16 is specifically defective in stimulating DDK phosphorylation of Mcm2.

FIG. 12A depicts 3 pmoles human DDK (Dbf4-Cdc7) incubated with 3 pmoles Mcm2 and γ-32P-ATP. The amount of Treslin added is indicated on top of the gel. The products were analyzed by SDS/PAGE followed by phosphorimaging. Molecular weight markers were used to identify the position of Mcm2 in the gel. A known amount of γ-32P-ATP was also spotted on the gel to quantify the amount of phosphate incorporation.

FIG. 12B depicts experiments similar to FIG. 10A but quantified and plotted as a function of Treslin input.

FIG. 12C depicts a similar experiment to FIG. 10A, except the products were analyzed by Western blot using antibody specific for phosphorylation of Mcm2 at S53 (left panel), S108 (middle panel), or Mcm2 (right panel).

FIGS. 12A-12F show that human Treslin stimulates human DDK phosphorylation of human Mcm2, promoting Mcm2 dissociation from Mcm5.

DETAILED DESCRIPTION OF THE PREFERRED EMBODIMENT

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

DDK phosphorylation of Mcm2 is a fundamental event in the cell cycle that triggers DNA replication. Whereas the current tumor marker Mcm2 is present at equal levels throughout the cell cycle, it was found herein that phosphorylated Mcm2 is present at substantially higher levels during S phase, when DNA replication is active. Since cancer cells spend a higher fraction of time in S phase compared to normal cells, cancer cells will likely have higher levels of DDK-phosphorylated-Mcm2 compared to normal cells. In addition, colorectal cancer cells have higher levels of DDK than normal cells.

Figure 5:
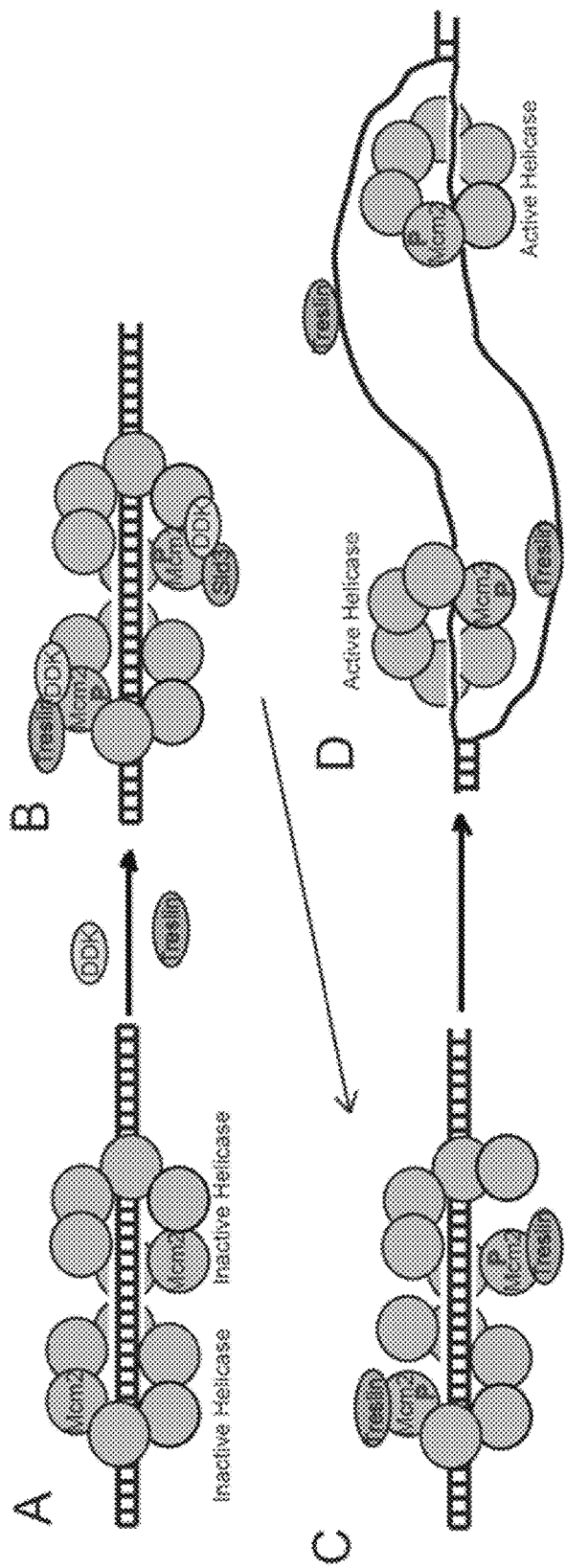
FIG. 5 shows that DDK-phosphorylated-Mcm2 is specific for the active helicase assembly that unwinds DNA at a replication fork. Panel A shows that in G1 phase, Mcm2 is unphosphorylated, and the helicase is inactive. Panel B shows that during S phase, DDK, acting in concert with Treslin, phosphorylates Mcm2 at serine 53 (P in the figure). Panel C shows that phosphorylation of Mcm2 at Serine 53 opens up the helicase ring (green circles), allowing the origin DNA to melt (black lines). Panel D shows that origin melting is required for activation of the helicase in S phase. Serine 53 is dephosphorylated during G2 (not shown). Thus, Mcm2-S53P is specific for cells that are undergoing active DNA replication, a general characteristic of cancer cells.

In an embodiment, the current invention is an assay for colon, rectal, and other cancers based on an antibody identification of a modified (phosphorylated) peptide at a specific site. More specifically, a novel post-translational modification of Mcm2 was identified and is described herein, wherein the residue of serines 53 and 108 is phosphorylated (Mcm2-S53P and Mcm2-S108P) (Bruck, I., and Kaplan, D. (2015) Conserved mechanism for coordinating replication fork helicase assembly with phosphorylation of the helicase. Proc Natl Acad Sci USA. 112, 11223-11228). It was found that a cell-cycle control protein, the Dbf4-dependent kinase (DDK), phosphorylates Mcm2 at serines 53 and 108 when stimulated by the replication initiation factor, Treslin (see FIG. 5; Bruck, I., and Kaplan, D. (2015) Conserved mechanism for coordinating replication fork helicase assembly with phosphorylation of the helicase. Proc Natl Acad Sci USA. 112, 11223-11228; and "Human Treslin stimulates human DDK phosphorylation of human Mcm2" of Example 1). The amino acid sequence of Treslin in SEQ ID NO:1, including amino acids 1 to 1,910; NCBI Accession No. Q7Z2Z1, version Q7Z2Z1.2 GI:156631024; UniProtKB/Swiss-Prot: Q7Z271). Amino acids 833-1133, 833-1267, 833-1910, 833-1000, 1000-1267, and 1000-1133 of SEQ ID NO:1 are each a phosphorylation-stimulating fragment of Treslin.

DDK is overexpressed in many human cancers, including colorectal cancer, suggesting that monitoring the phosphorylation of Mcm2 at serines 53 and 108 can detect early cancer with high sensitivity and specificity (Bruck, I., and Kaplan, D. (2015) Conserved mechanism for coordinating replication fork helicase assembly with phosphorylation of the helicase. Proc Natl Acad Sci USA. 112, 11223-11228). It was also found that the homologous modification (Mcm2-5170P) in budding yeast is required for DNA replication, and the modification occurs in cells during active DNA replication only (Hua, C., Zhao, G., Li, Y., and Bie, L. (2014) Minichromosome Maintenance (MCM) Family as potential diagnostic and prognostic tumor markers for human gliomas. *BMC Cancer* 14, 526). Thus, it was postulated that the human Mcm2-S53P modification is an improved cancer marker compared to human Mcm2.

In an embodiment, the current invention relates to an antibody specific for human Mcm2 that is phosphorylated at serine 53 (anti-Mcm2-S53P) and serine 108 (anti-Mcm2-S108P). This antibody was found to be overexpressed in colon cancer cell line HCT 116, as well as other cancer cell lines, compared to normal cells (see FIG. 6). Furthermore, the degree of overexpression of Mcm2-S53P Mcm2-S108P and is enhanced in cancer cells, including HCT 116 cells, compared to the gold standard, Mcm2 (see FIG. 6). Thus, the human Mcm2-S53P,S108P modification is an improved cancer marker compared to human Mcm2, and certain embodiments of the current invention provide improved screening assays for cancer and other diseases of cell proliferation by detecting this overexpression of Mcm2-S53P,S108P.

As seen in Brent E. Stead et al., Phosphorylation of Mcm2 modulates Mcm2-7 activity and affects the cell's response to DNA damage, Nucleic Acids Research, 2011, Vol. 39, No. 16, 6998-7008, the conventional art teaches away from the current findings, and as such, the current findings were highly unexpected. The current findings are further discussed in Irina Bruck and Daniel L. Kaplan, Conserved mechanism for coordinating replication fork helicase assembly with phosphorylation of the helicase, PNAS, Vol. 112, No. 36, 11223-11228 (Sep. 8, 2015), which is incorporated herein by reference in its entirety.

In an embodiment, the current invention relates to a screening assay (method) for identifying modulators of DDK using Treslin or an active fragment thereof, which provides a more robust, dynamic, and physiologically accurate signal than conventional methodologies. The assay of the invention comprises: (a) bringing together Treslin, or an active fragment thereof, DDK, an Mcm (e.g., Mcm2), adenosine triphosphate (ATP) or a molecule having a moiety that mimics ATP (i.e., an ATP mimic), and a candidate agent; and (b) detecting kinase activity. The aforementioned reactants may be brought into contact simultaneously or sequentially in any order under conditions that permit phosphorylation to take place in the absence of the influence of a phosphorylation inhibitor.

The aforementioned reactants may be brought together in a contacting step that can involves contacting, combining, or mixing the reactants. The contacting step may be carried out on a solid support, such as a reaction vessel, microvessel, tube, microtube, well, multi-well plate, or other solid support. In an embodiment of the invention, the solid support to be contacted with the reactants has an absorbent pad or membrane for lateral flow of the liquid medium to be assayed, such as those available from MILLIPORE Corp. (Bedford, Mass.), including, but not limited to, HI-FLOW PLUS membranes and membrane cards, and SUREWICK pad materials.

As indicated above, the contacting step and/or detecting step can be carried out on a solid support. The solid supports used may be those that are conventional for the purpose of assaying an analyte in a sample, and are typically constructed of materials such as cellulose, polysaccharide such as SEPHADEX, and the like, and may be partially surrounded by a housing for protection and/or handling of the solid support. The solid support can be rigid, semi-rigid, flexible, elastic (having shape-memory), etc., depending upon the desired application.

Any quantitative or qualitative method for detecting phosphorylation of Mcm by DDK can be used, such as that described in "Human Treslin stimulates human DDK phosphorylation of human Mcm2" of Example 1. In some embodiments, kinase activity is detected by detecting formation of phosphorylated Mcm with monoclonal or polyclonal antibody or antibody fragment (antigen-binding fragment) that is specific for Mcm2 that is phosphorylated at serine 53 or 108. Antibodies specific for phosphorylated Mcm specific residues such as serine 53 and 108 are commercially available (e.g., phospho Mcm2 (S53) antibody (rabbit polyclonal), catalog no. A300-756A, Bethyl Laboratories, Inc.; phospho Mcm2 (S108) antibody (rabbit polyclonal), catalog no. A300-094A, Bethyl Laboratories, Inc. anti-mcm2 (phospho S53) antibody [EP4120], rabbit monoclonal, Abcam, Inc.; anti-mcm2 (phospho S108) antibody [EPR4121], rabbit monoclonal, Abcam, Inc.). The target immunogen is the phosphor specific peptide corresponding to residues surrounding serine 53 or serine 108 of human Mcm2.

Another example of a method that may be used for detecting kinase activity in vitro quantitatively or qualitatively is a radioactive assay. In a radioactive assay, Treslin, DDK, and Mcm2 are mixed with a radioactive nucleotide such as γ-32P-ATP or γ-32P-GTP. The products are then analyzed by denaturing gel electrophoresis, and levels of the phosphorylated substrate, phospho-Mcm2, is quantified by phosphorimaging.

DDK activity can be determined in the presence of the candidate agent and in the absence of the candidate agent, and the measured levels of kinase activity can be compared to determine if there is a difference. The term "kinase activity" refers to the ability the kinase to catalyze the transfer of the terminal phosphate of ATP (or an ATP mimic) to substrates that usually contain a serine, threonine or tyrosine residue. A decrease in DDK activity in the presence of the candidate agent compared to its absence is indicative of an inhibitor and an increase in DDK activity in the presence of the agent compared to its absence is indicative of an inducer of DDK activity. Where phosphorylation of Mcm (e.g., Mcm2) is measured in the presence and absence of the candidate agent, a decrease in phosphorylated Mcm is indicative of an inhibitor and an increase in phosphorylated Mcm is indicative of an inducer of DDK activity. An appropriate control or standard may be selected and used by those of ordinary skill in the art.

Optionally, two or more candidate agents can be contacted with the other reactants simultaneously and their combined effect on kinase activity determined. Optionally, a candidate agent can be contacted with the other reactants in the presence and in the absence of a known modulator of kinase activity. In this way, agents that have an agonist or antagonist effect on a known modulator of kinase activity can be identified.

In some embodiments, a fragment of Treslin (a subsequence of the full-length 1,910 amino acid sequence of human Treslin) is used that has the capability to stimulate DDK phosphorylation of Mcm such as Mcm2, i.e., an active fragment of Treslin). In some embodiments, the active fragment of Treslin is selected from the group consisting of amino acids 833-1133, 833-1267, 833-1910, 833-1000, 1000-1267, 1000-1133 of the full-length sequence.

Examples of molecules having a moiety that mimics ATP (i.e., an ATP mimic) include imatinib (Gleevec), the engineered small molecule IRE1/PERK Activator (IPA) (43), or GTP plus water (44).

In some embodiments, one or more of the reactants (e.g., candidate agent, Treslin or an active fragment of Treslin, DDK, Mcm, ATP or an ATP mimic) are brought together in an isolated form. The term "isolated", as used herein with respect to compounds, such as the reactants of the methods of the invention and the components of the kits of the invention, refers to molecules that are isolated from cellular components, cell culture media, or chemical or synthetic precursors.

The method may be carried out as a cell-free assay, or as a cell-based assay by expressing one or more of the reactant polypeptides in a prokaryotic or eukaryotic host cell. Preferably, a human host cell is utilized for cell-based systems.

The candidate agent (potential DDK modulating agent) may be any composition of matter or class of molecule or molecules. For example, the candidate agent may be a biologic molecule such as a polypeptide, nucleic acid, carbohydrate, or lipid, an organic small molecule (compound), a complex, an extract, etc.

Candidate agents may be arrayed on a solid support, or multiple supports can be utilized, for multiplex detection or analysis. The term "arraying" refers to the act of organizing or arranging members of a library (e.g., an array of different candidate agents, and/or an array of the same candidate agent at different concentrations), or other collection, into a logical or physical array. Thus, an "array" refers to a physical or logical arrangement of, e.g., samples of candidate agent. A physical array can be any "spatial format" or "physically gridded format" in which physical manifestations of corresponding library members are arranged in an ordered manner, lending itself to combinatorial screening. For example, samples corresponding to individual or pooled members of a sample library can be arranged in a series of numbered rows and columns, e.g., on a multi-well plate. Similarly, candidate agents or other reactants in the screening method can be plated or otherwise deposited in microtitered, e.g., 96-well, 384-well, or 1536-well plates (or trays). Optionally, candidate agents or other reactants (e.g., Treslin or an active fragment of Treslin, DDK, Mcm, ATP or an ATP mimic) may be immobilized on the solid support.

Identification of DDK modulators (inhibitors or inducers), and other assays that are to be carried out on samples, can be carried out simultaneously or sequentially with the screening of other candidate agents, and may be carried out in an automated fashion, in a high-throughput format.

Optionally, when a candidate agent is identified as a DDK modulator based on its effect on DDK activity using the method of the invention, further steps may be carried out such as classifying the DDK modulator as an inhibitor or inducer of DDK activity. DDK inhibitors are potentially useful as agents for the treatment or prevention of a cell proliferation disorder such as cancer. The term "cancer"

generally refers to a diverse class of diseases that are commonly characterized by an abnormal proliferation of the diseased cells. A unifying characteristic in all known types of cancer is the acquisition of abnormalities in the genetic material of the cancer cell and its progeny. Once a cell becomes cancerous, it will proliferate without respect to normal limits, invading and destroying adjacent tissues, and may even spread to distant anatomic sites through a process called metastasis. These life-threatening, malignant properties of cancers differentiate them from benign tumors, which are self-limited in their growth and do not invade or metastasize.

Examples of cancer include, but are not limited to, cancer and/or tumors of the anus, bile duct, bladder, bone, bone marrow, bowel (including colon and rectum), breast, eye, gall bladder, kidney, mouth, larynx, lung, esophagus, stomach, testis, cervix, head, neck, ovary, mesothelioma, neuroendocrine, penis, skin, spinal cord, thyroid, vagina, vulva, uterus, liver, muscle, pancreas, prostate, blood cells (including lymphocytes and other immune system cells), and brain. In some embodiments, the cancer has elevated DDK relative to normal (non-cancerous) cells.

When a candidate agent has been identified as a DDK inhibitor, the method may further comprise evaluating the identified inhibitor for the ability to inhibit cancer cell growth (e.g., inhibiting cancer cell growth, inducing cancer cell death, reducing tumor size or inhibiting tumor growth) in vitro or in vivo. For example, a primary human or animal cancer cell or the cell of a cancer cell line may be contacted with the identified inhibitor in vitro and its effect(s) on the human or animal cancer cell evaluated (41, 42). Alternatively, or in addition to the in vitro evaluation, a cancer cell can be contacted with the identified inhibitor in vivo. For example, the identified inhibitor may be administered to an animal model bearing the cancer cell (e.g., cancer xenograft models), and the effect of the inhibitor on the cancer cell and/or on the animal may be evaluated (42). The effect of the identified inhibitor on cancer cells can be determined in the presence or absence of one or more other anti-cancer agents in combination (simultaneously or consecutively) in vitro and/or in vivo.

As used herein, the term "tumor" refers to all neoplastic cell growth and proliferation, whether malignant or benign, and all pre-cancerous and cancerous cells and tissues. For example, a particular cancer may be characterized by a solid mass tumor. The solid tumor mass, if present, may be a primary tumor mass. A primary tumor mass refers to a growth of cancer cells in a tissue resulting from the transformation of a normal cell of that tissue. In most cases, the primary tumor mass is identified by the presence of a cyst, which can be found through visual or palpation methods, or by irregularity in shape, texture or weight of the tissue. However, some primary tumors are not palpable and can be detected only through medical imaging techniques such as X-rays (e.g., mammography), or by needle aspirations. The use of these latter techniques is more common in early detection. Molecular and phenotypic analysis of cancer cells within a tissue will usually confirm if the cancer is endogenous to the tissue or if the lesion is due to metastasis from another site. The term "tumor" is inclusive of solid tumors and non-solid tumors.

Optionally, the method may further comprise manufacturing the candidate agent that is indicated to be a DDK inhibitor as a pharmaceutical composition and/or marketing the candidate agent that is indicated to be a DDK inhibitor as a treatment for one or more cancers. As used herein, a "pharmaceutical composition" refers to a preparation of one or more of the identified DDK inhibitors as active ingredients with other substances such as physiologically suitable carriers and excipients. The purpose of a pharmaceutical composition is to facilitate administration of an agent to a human or animal subject.

Techniques for formulation and administration of drugs may be found in the latest edition of "Remington's Pharmaceutical Sciences," Mack Publishing Co., Easton, Pa., which is herein fully incorporated by reference.

Suitable routes of administration for agents identified as DDK inhibitors and the pharmaceutical compositions containing them may, for example, include oral, rectal, transmucosal, especially transnasal, intestinal, or parenteral delivery, including intramuscular, subcutaneous, and intramedullary injections, as well as intrathecal, direct intraventricular, intravenous, intraperitoneal, intranasal, or intraocular injections.

As used herein, the term "active ingredient" refers to the agent accountable for the intended biological effect (e.g., decrease in DDK activity, or inhibition of cancer cell growth). As used herein, the phrases "physiologically acceptable carrier" and "pharmaceutically acceptable carrier," which may be used interchangeably, refer to a carrier or a diluent that does not cause significant irritation to the subject and does not abrogate the biological activity and properties of the administered agent.

As used herein, the term "excipient" refers to an inert substance added to a pharmaceutical composition to further facilitate administration of an active ingredient. Examples of excipients include, but are not limited to, calcium carbonate, calcium phosphate, various sugars and types of starch, cellulose derivatives, gelatin, vegetable oils, and polyethylene glycols.

Pharmaceutical compositions of the present invention may be manufactured by processes well known in the art, e.g., by means of conventional mixing, dissolving, granulating, dragee-making, levigating, emulsifying, encapsulating, entrapping, or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations that can be used pharmaceutically. Proper formulation is dependent upon the route of administration chosen. Determination of an effective amount is well within the capability of those skilled in the art, especially in light of the detailed disclosure provided herein.

For any preparation used in the methods of the invention, the dosage or the effective amount can be estimated initially from in vitro and cell culture assays (e.g., proliferation assay). For example, a dose can be formulated in animal models to achieve a desired concentration or titer. Such information can be used to more accurately determine useful doses in humans.

In certain embodiments, the invention also provides kits comprising Treslin, or active fragments thereof, and one or more additional components, which may be used, for example, for carrying out methods of the invention, i.e., identifying inhibitors and inducers of DDK. In some embodiments, the kit comprises Treslin, or an active fragment of Treslin as described above, with one or more of the following: DDK, mini-chromosome maintenance protein (Mcm), adenosine triphosphate (ATP) or a molecule having a moiety that mimics ATP (ATP mimic) as described above, or an antibody or antibody fragment that is specific for the Mcm (e.g., an antibody or antibody fragment that is specific for phosphorylated at serine 53 or 108). In some embodiments, two or more of the foregoing components are present in the kit. In some embodiments, three or more components of the foregoing components are present in the kit. In some embodiments, all of the foregoing components are present in the kit. The kits may optionally provide additional components, such as buffers and instructions for use of any components of the kit in identifying DDK modulators.

In some embodiments, one or more of the components of the kit (e.g., candidate agent, Treslin or an active fragment of Treslin, DDK, Mcm, ATP or an ATP mimic, antibody or antibody fragment) is in an isolated form.

In some embodiments, the kit includes a fragment of Treslin (a sub-sequence of the full-length 1,910 amino acid sequence of human Treslin) that has the capability to stimulate DDK phosphorylation of Mcm such as Mcm2, i.e., an active fragment of Treslin). In some embodiments, the active fragment of Treslin is selected from the group consisting of amino acids 833-1133, 833-1267, 833-1910, 833-1000, 1000-1267, 1000-1133 of the full-length sequence. In some embodiments, the kit includes an antibody or antigen-binding fragment thereof (antibody fragment) that is specific for phosphorylated Mcm. In some embodiments, the antibody or antibody fragment is specific for human Mcm2 that is phosphorylated serine 53 or serine 108. In some embodiments, the kit includes an ATP mimic. Examples of molecules having a moiety that mimics ATP (i.e., an ATP mimic) include imatinib (Gleevec), the engineered small molecule IRE1/PERK Activator (IPA), or GTP plus water. In some embodiments, the kit includes a radioactive nucleotide such as γ-32P-ATP or γ-32P-GTP for detection of kinase activity.

Each component of the kit (e.g., Treslin or an active fragment of Treslin, DDK, Mcm, ATP or an ATP mimic, antibody or antibody fragment), or a combination of two or more components, may be contained in a container. It should be appreciated that the kits of the invention are not limited to any particular container configuration. The container(s) can be constructed and arranged and stored, and their contents dispensed, in any of numerous ways within the scope of the invention. For example, in some embodiments, the kit includes a tray or other housing with one or more cavities of desirable geometries for receiving one or more components of the kit. Containers for holding components of the kit can be rigid (such as canisters) or soft (such as bags or pouches), as needed or desired. Materials for constructing containers for reagents in various physical states are known in the art. In some embodiments, the container(s) and housing is plastic, such as polypropylene. The kit is preferably packaged for ease of handling and use by the individual(s) conducting the screening assay. The kit is preferably sealed and sterilized.

The following are examples that illustrate procedures for or results from practicing certain embodiments of the current invention. These examples should not be construed as limiting. All percentages are by weight and all solvent mixture proportions are by volume unless otherwise noted.

Example 1

The replication fork helicase unwinds double-stranded DNA at a replication fork, and assembly and activation of this helicase are tightly controlled. Described herein is a biological mechanism to link two essential functions related to helicase assembly and activation. Sld3, a protein required for initiation of DNA replication, coordinates the assembly of the replication fork helicase with the chemical modification of a helicase protein subunit. This chemical modification is important for subsequent activation of the helicase.

DDK phosphorylates Mcm2 during S phase in yeast, and Sld3 recruits Cdc45 to Mcm2-7. DDK-phosphoryled-Mcm2 is shown herein to preferentially interact with Cdc45 in vivo, and Sld3 stimulates DDK phosphorylation of Mcm2 by 11-fold. A mutation of Sld3, Sld3-m16, was identified to be specifically defective in stimulating DDK phosphorylation of Mcm2. Wild-type expression levels of sld3-m16 result in severe growth and DNA replication defects. Cells expressing sld3-m16 exhibit no detectable Mcm2 phosphorylation in vivo, reduced RPA-ChIP signal at an origin, and diminished GINS association with Mcm2-7. Treslin, the human homolog of Sld3, stimulates human DDK phosphorylation of human Mcm2 by 15-fold. DDK phosphorylation of human Mcm2 decreases the affinity of Mcm5 for Mcm2, suggesting a potential mechanism for helicase ring opening. These data suggest a conserved mechanism for replication initiation: Sld3/Treslin coordinates Cdc45 recruitment to Mcm2-7 with DDK phosphorylation of Mcm2 during S phase.

It is shown herein that DDK-phosphorylated-Mcm2 preferentially interacts with Cdc45 in vivo compared to Mcm2 (all Mcm2 in cell, phosphorylated and unphosphorylated), suggesting that Cdc45 recruitment to Mcm2-7 is correlated with DDK phosphorylation of Mcm2. It is also shown that Sld3 substantially stimulates DDK phosphorylation of Mcm2 in vitro. A mutant of Sld3, sld3-m16, was identified to be defective in the stimulation of DDK phosphorylation of Mcm2. When sld3-m16 is expressed in budding yeast cells, a dominant negative severe growth defect is observed that is bypassed by mcm5-bob1. Wild-type expression levels of sld3-m16 confer a growth and DNA replication defect, with decreased DDK phosphorylation of Mcm2. Furthermore, expression of sld3-m16 results in diminished RPA-ChIP signal at an origin, and decreased GINS interaction with Mcm2-7. Furthermore, human Treslin substantially stimulates DDK phosphorylation of Mcm2 at serines 53 and 108. Finally, a mutant of human Mcm2 that mimics DDK-phosphorylated-Mcm2 exhibits diminished interaction with human Mcm5, suggesting a mechanism for 'gate' opening. As such, it is concluded that Sld3 coordinates helicase phosphorylation with helicase assembly.

Materials and Methods

Generally, antibodies were obtained from a commercial supplier, and plasmids and proteins were generated using established methods. Yeast strains were generated from a supplied material supplied, and kinase labeling of proteins was performed as described. DDK reactions were performed at 30° C. for 60 minutes. Yeast dilutions were performed in 1:10 dilutions on agar plates. FACS analysis was performed with propidium iodide staining. Chromatin immunoprecipitation was performed with crosslinking reagent as previously described. Co-immunoprecipitation analyses were performed with no crosslinking agent and no hydroxyurea as described. Specifics of the materials and methods are described as follows.

Antibodies.

Antibodies directed against RPA were purchased from Pierce. Antibodies directed against Mcm2-1-160 and Mcm2-161-173-phosphoserine-164-phosphoserine 170 were validated as described (21). Antibodies directed against the Flag, HA, or His epitopes were commercially purchased. Antibodies directed against human Mcm2-phosphoserine-40/41, Mcm2-phosphoserine-53, or Mcm2-phosphoserine-108 were commercially purchased (Bethyl Laboratories). Antibodies against Mcm4-S171-phosphoserine-S174-phosphoserine were produced by Pierce.

Yeast Strains.

The sld3-7 td degron strain was obtained via gift. The epitope tags were generated using reagents obtained via gift. The mcm5-bob1 mutation was introduced into the yeast strain by allelic replacement of the MCM5 endogenous locus (21). MDY104 BY4743 (MATa/α his3Δ1his3Δ1leu2Δ0/leu2Δ0ura3Δ0/ura3Δ0 MET15/met15Δ0LYS2/lys2Δ0 MCM2/mcm2AA (Stead et al. *Nucleic Acids Research*, 2011, 39:16 pp 6998-7008).

MDY139 MATa his3Δ1/his3Δ1 leu2Δ0/leu2Δ0 MET15/met15Δ0 LYS2/lys2Δ0 mcm2AA (Ura3). YMK517(2889) MATa ade2-1 ura3-1 his3-11,15 trp1-1 leu2-3,112 can1-100 GAL-UBR19HIS3 sld3-7td(kanMX) mcm4:Mcm4-5FLAG (k.1. TRP1), cdc45::Cdc45-6HA(hphNT), psf2::PSF2-5FLAG (hphNT), dpb11::DPB 11-V5(Ura3)

YKL69 MATa ade2-1 ura3-1 his3-11,15 trp1-1 leu2-3,112 can1-100 GAL-UBR19HIS3 MCM2::mcm2-td(Ura3) mcm5::mcm5 bob1(TRP1).

Plasmids.

cDNA for human Mcm2, Mcm5, Mcm6, and Cdc45 were obtained via gift. The genes were re-cloned form baculovirus vector to pET33b (PKA-Mcm5, PKA-Mcm6, or PKA-Cdc45) or pET41 (GST-Mcm2, wild-type and mutants). Human Treslin cDNA was obtained via gift. Full-length human Treslin was re-cloned into pET33b (PKA-Treslin). cDNA for human Dbf4 and Cdc7 were obtained from THERMO SCIENTIFIC. Dbf4 was cloned into pET41a, and Cdc7 was cloned in to pETDuet. The following plasmids were used for experiments described herein: pIB401 (pRS415 CEN6/ARSH4 GALS::SLD3-6His LEU2), pIB402 (pRS415 CEN6/ARSH4 GALS::sld3 S556A, H557A,S558A,T559A-6His LEU2).

Protein Purification.

Yeast Mcm2-7 subunits and complex, DDK, Sld3, Cdc45, Dpb11, and CDK were purified as described (15, 16, 21, 26). Human Mcm2, Mcm5, Mcm5, Cdc45, DDK (co-expression of GST-Dbf4 and Cdc7), and Treslin were subjected to nickel chromatography, anion exchange (Q SEPHAROSE) and gel filtration. GST-Mcm2, wild-type and mutants, and DDK were subjected to additional glutathione SEPHAROSE (GE healthcare) chromatography. Protein Kinase A was obtained via gift.

Kinase Labeling of Proteins.

PKA, CDK, and DDK labeling of proteins was performed as described (16, 26, 30). Proteins containing a PKA tag at the N-terminus were radiolabeled in a reaction volume of 100 μl that contained 20 mM PKA-tagged protein in kinase reaction buffer (5 mM Tris-HCl, pH 8.5, 10 mM $MgCl_2$, 1 mM DTT, 500 μM ATP, 500 μCi [$\gamma$-$^{32}$P]-ATP containing 5 mg PKA, DDK, or CDK. Reactions were incubated for 1 hour at 30° C. The kinase was then removed from the mixture by affinity chromatography. DDK phosphorylation assays were performed as described (30). Briefly, DDK was added to Mcm2 in the presence of ATP and different amounts of Sld3 for 1 hour at 30° C.

Yeast Dilutions.

10-fold serial dilutions were performed as described (26).

Fluorescence Activated Cell Sorting (FACS Analysis).

FACS analysis was performed as described (26). $6\times10^6$ cells/ml were treated with α-factor (Zymo Research) for 3 hours. After extensive washes and the addition of 50 μg/ml Pronase, the cells were incubated for the indicated time. Cell cycle progression was then analyzed by flow cytometry (FACS) stained with propidium iodide with FACSARIA.

Chromatin Immunoprecipitation.

Chromatin immunoprecipitation was performed as described (21). $6\times10^6$ cells/ml were treated with α-factor (Zymo Research) for 3 hours. Following extensive washes and the addition of 50 μg/ml Pronase, cells were further incubated for 0 or 20 minutes at the indicated temperature of the experiment. PCR was performed with [$^{32}$P-α]-dCTP as a component of the PCR reaction in order to quantify the amplified DNA product. Formaldehyde cross-linked cells were lysed with glass beads in a Bead Beater. DNA was fragmented by sonication (Branson 450, 6 cycles of 15 seconds each). Antibody and magnetic protein A beads were added to the cleared lysate to immunoprecipitate the DNA. Immunoprecipitates were then washed extensively to remove nonspecific DNA. Eluted DNA was subjected to PCR analysis using primers directed against ARS305, ARS306, or a region midway between ARS305 and ARS306 as described (21). The radioactive band in the agarose gel, representing specific PCR amplified DNA product, was quantified by phosphorimaging and normalized by a reference standard run in the same gel. The reference standard was a PCR reaction accomplished with known quantity of template DNA replacing immunoprecipitate.

Co-Immunoprecipitation.

Co-immunoprecipitation was performed as described (21). $6\times10^6$ cells were treated with α-factor (Zymo Research) for 3 hours. Cells were then subjected to extensive washes, followed by the addition of 50 μg/ml Pronase. Cells ($4\times10^8$) were collected and lysed at 4° C. with glass beads (BeadBeater) in IP buffer (100 mM Hepes-KOH pH 7.9, 100 mM potassium acetate, 10 mM magnesium acetate, 2 mM NaF, 1 mM PMSF, 0.1 mM $Na_3VO_4$, 10 mM β-glycerophosphate, 1% Triton X-100, leupeptin, pepstatin, 1% protease inhibitor cocktail, 1× Complete protease inhibitor cocktail without EDTA. Lysed material was treated with 200 U of Benzonase nuclease on ice for 1 hour. Clarified extract was then mixed with 2 μl of specified antibody and rotated for 2 hours in the cold room, and then 5 μl of Dynabeads Protein A beads equilibrated with IP buffer, were added and further incubated for 2 hours. Beads were then washed two times with 1 ml of IP buffer and re-suspended in SDS-sample buffer. Western analysis was performed using the ODYSSEY system.

GST-Pulldown.

The GST-Pulldown assays were performed as described (21). GST-pulldown reactions were in a volume of 100 μl and contained GST-tagged protein in GST-binding buffer (40 mM Tris-HCl, pH 7.5, 100 mM NaCl, 0.1 mM EDTA, 10% glycerol, 0.1% Triton X-100, 1 mM DTT, 0.7 mg/ml pepstatin, 0.1 mM PMSF, and 0.1 mg/ml BSA) and varying amounts of radiolabeled protein as described in each Figure. Reactions were incubated at 25° C. for 1 hour. Following incubation, reactions were added to 40 μl glutathione SEPHAROSE and gently mixed. Binding of GST-tagged protein to the protein was performed for 20 minutes with gentle mixing every two minutes. When the binding was complete, the beads were allowed to settle, the supernatant was removed, and the glutathione beads were washed two times with 0.5 ml GST-binding buffer. After the last wash, 30 μl of 5×SDS sample buffer were added to each reaction, and the samples were heated to 95° C. for 10 minutes. Samples (20 μl) were then analyzed by SDS-PAGE followed by phosphorimaging and quantitation.

Results

Strain Harboring Constitutively-Expressed-DDK-Dead-Mcm2-Mutant (Mcm2-S164A,S170A Expressed from Native Promoter) Exhibits Suppression.

The current inventors previously found that induced-expression of mcm2-S164A,S170A, which is a DDK-dead mutant of mcm2, confers a dominant-negative severe growth defect in budding yeast. Expression of mcm2-S164A,S170A, when incorporated into the genome under constitutive expression by its native promoter, exhibited a defect only when exposed to DNA damaging agents such as MIMS (27, 28). Given the dominant-negative phenotype observed, it was predicted that this native-promoter-strain harbored a suppressor mutation. Thus, the native-promoter-strain was obtained, and the mcm2-S164A,S170A gene was expressed from a galactose-inducible promoter. Whereas wild-type yeast cells exhibit a severe growth defect upon expression of mcm2-5164A,S170A (FIG. 7A & (21)), the native-promoter-strain exhibited no growth defect (FIG. 7B). These results suggest that the native-promoter-strain harbors a suppressor mutation, explaining the differences in results. These data also lend further support that expression of mcm2-S164A,S170A confers a dominant negative growth defect under normal growth conditions, and DDK phosphorylation of Mcm2 is required for growth under normal conditions.

Mcm2 Association with Cdc45 is Correlated with DDK Phosphorylation of Mcm2 During S Phase.

Figure 1A:
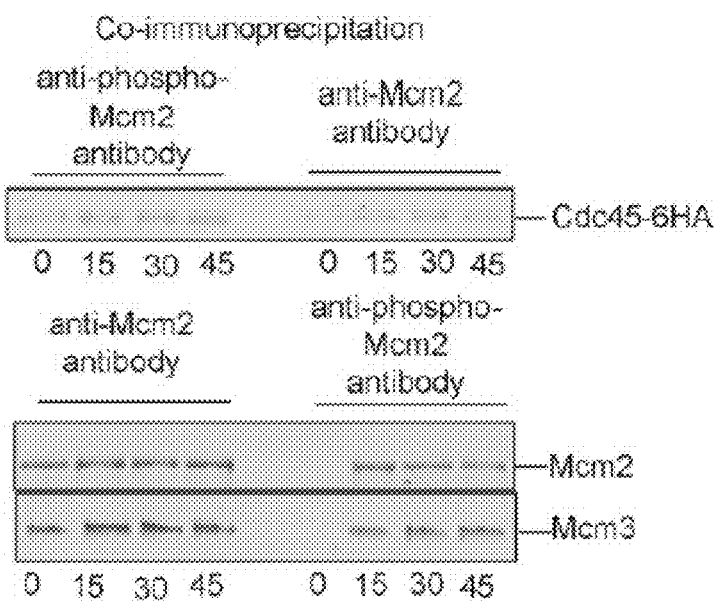
FIG. 1A depicts co-immunoprecipitation analysis of wild-type budding yeast cells using antibody against the N-terminus of Mcm2 (residues 1-160) or an antibody directed against the DDK-phosphorylated Mcm2 (anti-phosphoserines 164 and 170). Cells were arrested in $G_1$ with α-factor and release into medium lacking α-factor for the times incubated.

Mcm2-7 complexes are loaded in excess relative to those Mcm2-7 complexes in late M phase and $G_1$ relative to those Mcm2-7 complexes that unwind DNA in S phase (29). While there are many steps involved in activation of the helicase, one key to Mcm2-7 activation is the association of Mcm2 with Cdc45 (25), while a second key is the DDK phosphorylation of Mcm2 (20). There was a question as to whether these two events were correlated. Thus, cells in $G_1$ were synchronized with α-factor, and then released into medium lacking α-factor for 0, 15, 30, and 45 minutes. Next, wild-type yeast cell extracts were immunoprecipitated with antibody directed against Mcm2 (anti-Mcm2-1-160, insensitive to DDK phosphorylation of Mcm2 (21)), or antibody directed against phospho-Mcm2 (anti-mcm2-phospho-S164-phospho-S170, sensitive to DDK phosphorylation of Mcm2 (21)). The immunoprecipitate was then examined by Western analysis using antibodies directed against Cdc45-6HA (FIG. 1A). Anti-phospho-Mcm2 antibody yielded a substantially stronger signal at 15, 30, and 45-minute time points compared to Anti-Mcm2. These data suggest that DDK phosphorylation of Mcm2 is correlated with Cdc45 attachment to Mcm2 during S phase. While a simple explanation is that DDK phosphorylation of Mcm2 increases the affinity of Mcm2 for Cdc45, previously published in vitro experimental data argue against this idea (21). Thus, DDK phosphorylation of Mcm2 does not directly cause Cdc45 to associate with Mcm2-7. It was therefore a question as to whether Sld3, which recruits Cdc45 to Mcm2-7 (2), plays a role in coordinating Cdc45 recruitment to Mcm2-7 with DDK phosphorylation of Mcm2.

Sld3 Substantially Stimulates DDK Phosphorylation of Mcm2 In Vitro.

Figure 1B:
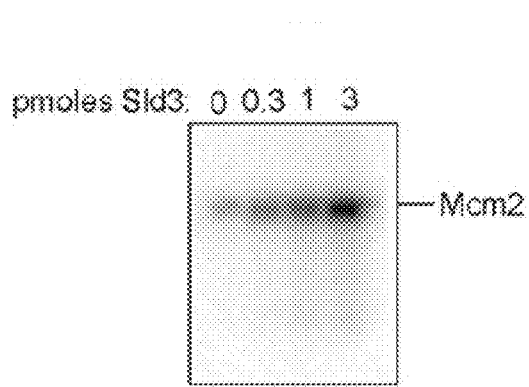
FIG. 1B shows that 3 pmoles budding yeast DDK (Dbf4-Cdc7) was incubated with 3 pmoles Mcm2 and $\gamma$-$^{32}$P-ATP as described below. The amount of Sld3 added is indicated on top of the gel. The products were analyzed by SDS/PAGE followed by phosphorimaging. Molecular weight markers were used to identify the position of Mcm2 in the gel. A known amount of γ-32P-ATP was also spotted on the gel to quantify the amount of phosphate incorporation.
Figure 1C:
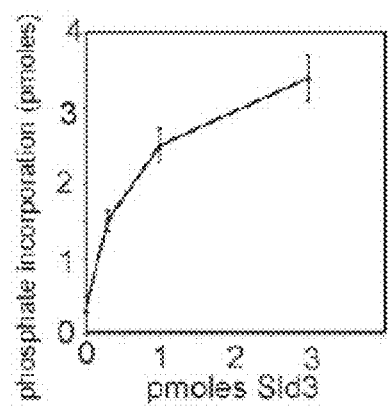
FIG. 1C depicts experiments similar to FIG. 1B but quantified and plotted.
Figure 1D:
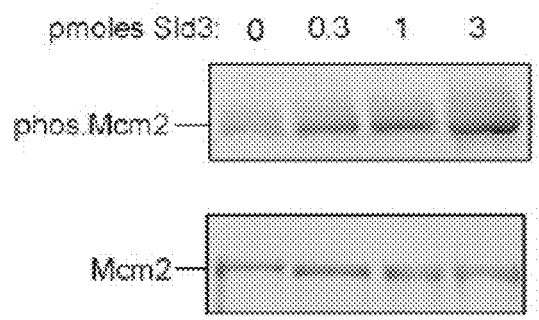
FIG. 1D depicts an experiment similar to FIG. 1B, except the products were analyzed by Western using antibody specific for DDK phosphorylation of Mcm2 at S164 and S170, as described previously (21).
Figure 1E:
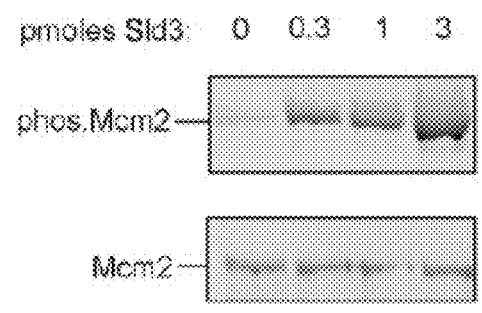
FIG. 1E is similar to FIG. 1D, except the Mcm2-7 complex was used as a substrate. Overall.

DDK phosphorylates Mcm2 weakly in vitro (30), and it was next investigated if Sld3 stimulates this phosphorylation event. DDK was incubated with Mcm2, γ-32P-ATP, and increasing amounts of Sld3. The results were analyzed by SDS/PAGE followed by phosphorimaging and quantitation (FIGS. 1B and 1C). A substantial, 11-fold increase in DDK phosphorylation of Mcm2 was found with the addition of Sld3. These data suggest that Sld3 substantially stimulates DDK phosphorylation of Mcm2 in vitro. It was next examined whether the anti-phospho-Mcm2 antibody, which recognizes Mcm2-phosphoserine-164-phosphoserine-170, detects higher levels of DDK phosphorylation of Mcm2 by Western analysis, using Mcm2 as a substrate (FIG. 1D). Indeed, there is a substantial increase in phospho-antibody signal, suggesting that Sld3 stimulates DDK phosphorylation of Mcm2 by stimulating phosphorylation at S164/S170. The experiment reported in FIG. 1D was repeated, but Mcm2-7 complex were used as a substrate (FIG. 1E). Western analysis demonstrates substantial stimulation of the DDK-phosphorylation of Mcm2 at S164/170. These data suggest that Sld3 substantially stimulates DDK phosphorylation of Mcm2 when Mcm2 is incorporated into the Mcm2-7 complex.

Sld3-m16 is a Separation-of-Function Mutant that is Specifically Defective in Stimulating DDK Phosphorylation of Mcm2

Figure 8A:
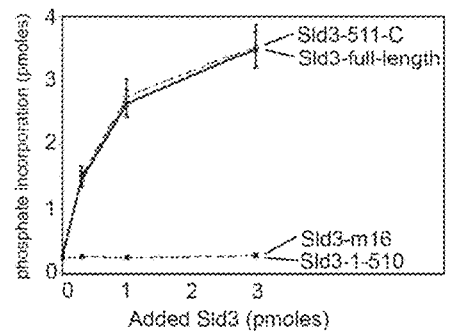
FIG. 8A depicts experiments similar to those in FIGS. 1B and 1C, except Sld3-full-length, Sld3-511-C, Sld3-1-510, or Sld3-m16 were used.

The next task was to identify a separation-of-function mutant of Sld3 that is specifically defective in stimulating DDK phosphorylation of Mcm2, in order to pursue in vivo studies. Sld3 was divided into two fragments: an N-terminal fragment (Sld3-1-510) and a C-terminal fragment (Sld3-511-C). The phosphorylation assay described in FIGS. 1C and 1D was then repeated. The C-terminal region of Sld3 (Sld3-511-C) was found to function like wild-type Sld3 in stimulating DDK phosphorylation of Mcm2, while the N-terminal region of Sld3 (Sld3-1-510) had no effect (FIG. 6A). These results suggest that the C-terminal region of Sld3 is responsible for DDK phosphorylation of Mcm2. Site directed mutagenesis was then performed in the 511-C region of Sld3. A large number of mutants were screened, and the sixteenth mutant tried, Sld3-m16 (Sld3-S556A, H557A,S558A,T559A), exhibited a substantial defect in stimulating DDK phosphorylation of Mcm2 (FIG. 8A).

Figure 8B:
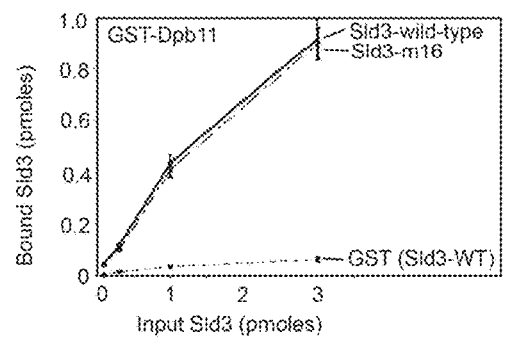
FIG. 8B shows that 3 pmoles GST-Dpb11 was used to pull-down CDK-phosphorylated and radiolabeled Sld3-wild-type or Sld3-m16. The products of the pulldown were analyzed by SDS/PAGE followed by phosphorimaging. Repeated experiments were quantified, averaged, and plotted.
Figure 8C:
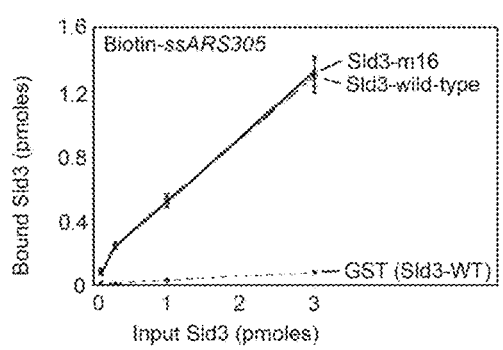
FIG. 8C is similar to FIG. 6B, except 3 pmoles biotin-ssARS305 (an 80mer origin ssDNA described in (16)) was used with streptavidin beads to pull down Sld3.
Figure 8D:
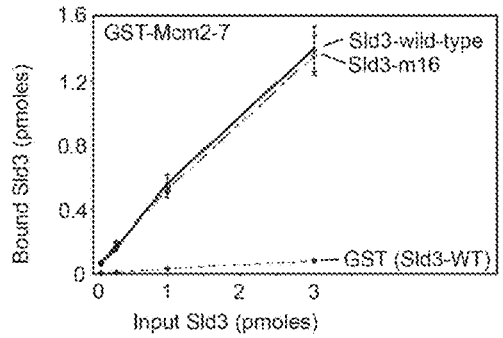
FIG. 8D is also similar to FIG. 6B, except 3 pmoles GST-Mcm2-7 was used to pull down Sld3.
Figure 8E:
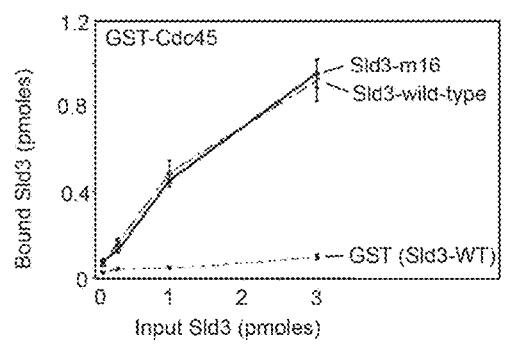
FIG. 8E is also similar to FIG. 6B, except 3 pmoles GST-Cdc45 was used to pull down Sld3. Overall.

It was then determined whether Sld3-m16 was specifically defective for stimulating DDK phosphorylation of Mcm2, or whether it is defective in some other known function of Sld3. CDK-phosphorylated Sld3 binds Dpb11 (9, 10). The interaction between CDK-phosphorylated Sld3-m16 and Dpb11 was thus determined, and it was found that it bound like wild type Sld3 (FIG. 8B). Sld3 is also known to bind T-rich origin ssDNA, Mcm2-7, and Cdc45 (16, 23). Therefore, the interaction between Sld3-m16 and origin ssDNA (FIG. 8C), Mcm2-7 (FIG. 8D), or Cdc45 (FIG. 8E) was determined. In each instance, Sld3-m16 bound to ssDNA, Mcm2-7, or Cdc45 like wild-type Sld3. These data suggest that Sld3-m16 is a separation-of-function-mutant that is specifically defective in stimulating DDK phosphorylation of Mcm2.

Expression of Sld3-m16 Results in a Dominant-Negative Severe Growth Defect with Substantially Decreased Phosphorylation of Mcm2.

Figure 2A:
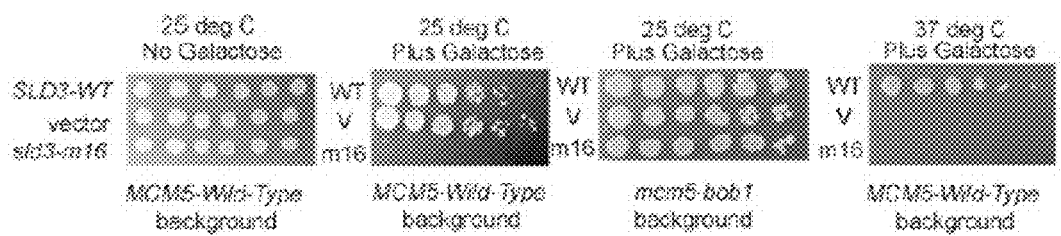
FIG. 2A depicts a 10-fold serial dilution analysis of budding yeast sld3-7 td (sld3-temperature-sensitive degron) cells expressing SLD3-WT, vector, or sld3-m16 from the GAL-S plasmid inducible promoter system (pRS415). The growth conditions are described at the top of the figure, and the strain background is described at the bottom of the figure.
Figure 2B:
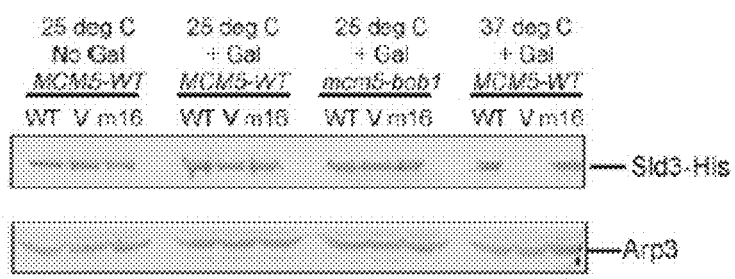
FIG. 2B is a Western analysis of whole cell extracts from cells used in FIG. 2A, probing with antibody directed against Sld3.

An sld3-7 td strain was obtained for in vivo studies (3). In this strain, the genomic copy of SLD3 is degraded at the restrictive temperature (37° C.). Given that expression of mcm2-S164A,S170A confers a dominant-negative severe growth defect in budding yeast cells (21), it was anticipated that expression of sld3-m16 may also confer a dominant negative phenotype. Thus, sld3-m16 was expressed from the GAL S inducible expression system, a low copy inducible expression system, and the concentration of galactose was varied until wild-type levels of Sld3-m16 was achieved at the restrictive temperature (FIG. 2B). In the absence of galactose, no sld3-m16 is induced, and the cells grow like wild-type SLD3 (FIG. 2A, first panel). However, once galactose is added at the permissive temperature (25° C.), the cells exhibit a severe growth defect (FIG. 2A, second panel). These results suggest that expression of sld3-m16 results in a dominant-negative severe growth defect.

The same experiment was then performed, but in a mcm5-bob1 genetic background, since the mcm5-bob1 mutation suppresses the growth defect conferred by expression of mcm2-S164A,S170A (21). Indeed, the mcm5-bob1 mutation suppressed the growth defect conferred by expression of sld3-m16 (FIG. 2A, third panel), suggesting that the mechanism for growth inhibition conferred by expression of mcm2-S164A,S170A or sld3-m16 is similar. sld3-m16 was next expressed at the restrictive temperature at wild-type expression levels (FIG. 2B), and a severe growth defect was found (FIG. 2A, fourth panel). These data suggest that under normal growth conditions and wild-type expression of sld3-m16, cell growth is severely impaired.

Figure 2C:
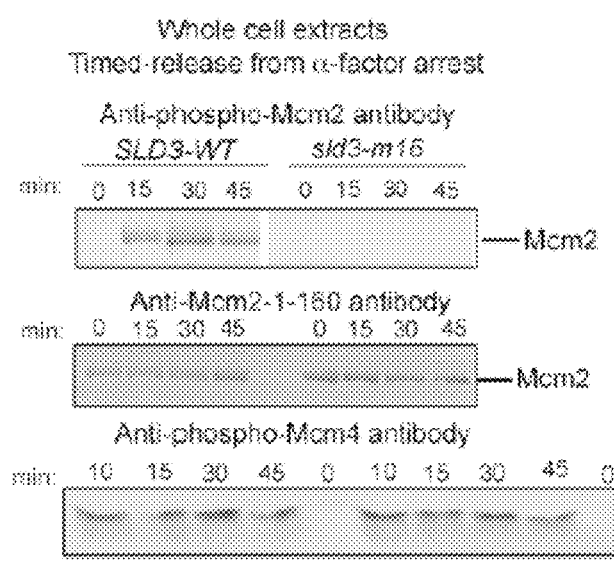
FIG. 2C is similar to 2B, except probing with antibody directed against DDK-phosphorylated Mcm2. A white line in the image indicates where the image was spliced from different gels.
Figure 2D:
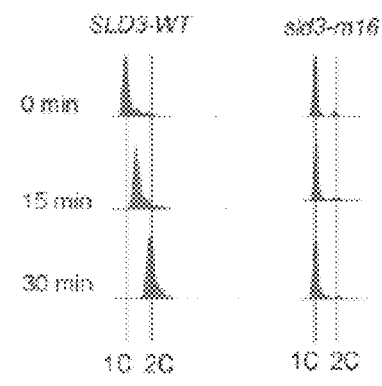
FIG. 2D depicts a FACS analysis of cells described in FIG. 2A, using propidium iodide as a stain for DNA content. Overall.

For the cells examined at the restrictive temperature, it was examined whether there is a defect in Mcm2 phosphorylation by DDK (FIG. 2C). Whole cell extract analysis was performed, followed by blotting with antibody directed against DDK-phosphorylated Mcm2 (Mcm2-phospho-serine-164-phosphoserine-170). Cells in $G_1$ were synchronized with α-factor, and then released in the absence of α-factor with no hydroxyurea for 0, 15, 30, and 45 minutes. Whereas wild-type cells exhibited an increase in phospho-Mcm2 as cells entered S phase, cells expressing sld3-m16 exhibited no detectable levels of phospho-Mcm2 during S phase. These results suggest that expression of sld3-m16 confers a substantial decrease in phospho-Mcm2 expression (FIG. 2C). This result is specific for phosho-Mcm2 expression, and not phospho-Mcm4 expression (FIG. 2C). Next, it was examined whether there was a defect in DNA replication for cells examined at the restrictive temperature, and indeed slow progression was seen through S phase for cells expressing sld3-m16 (FIG. 2D).

Expression of Sld3-m16 Results in Decreased RPA-ChIP Signal at an Origin of Replication.

Figure 9:
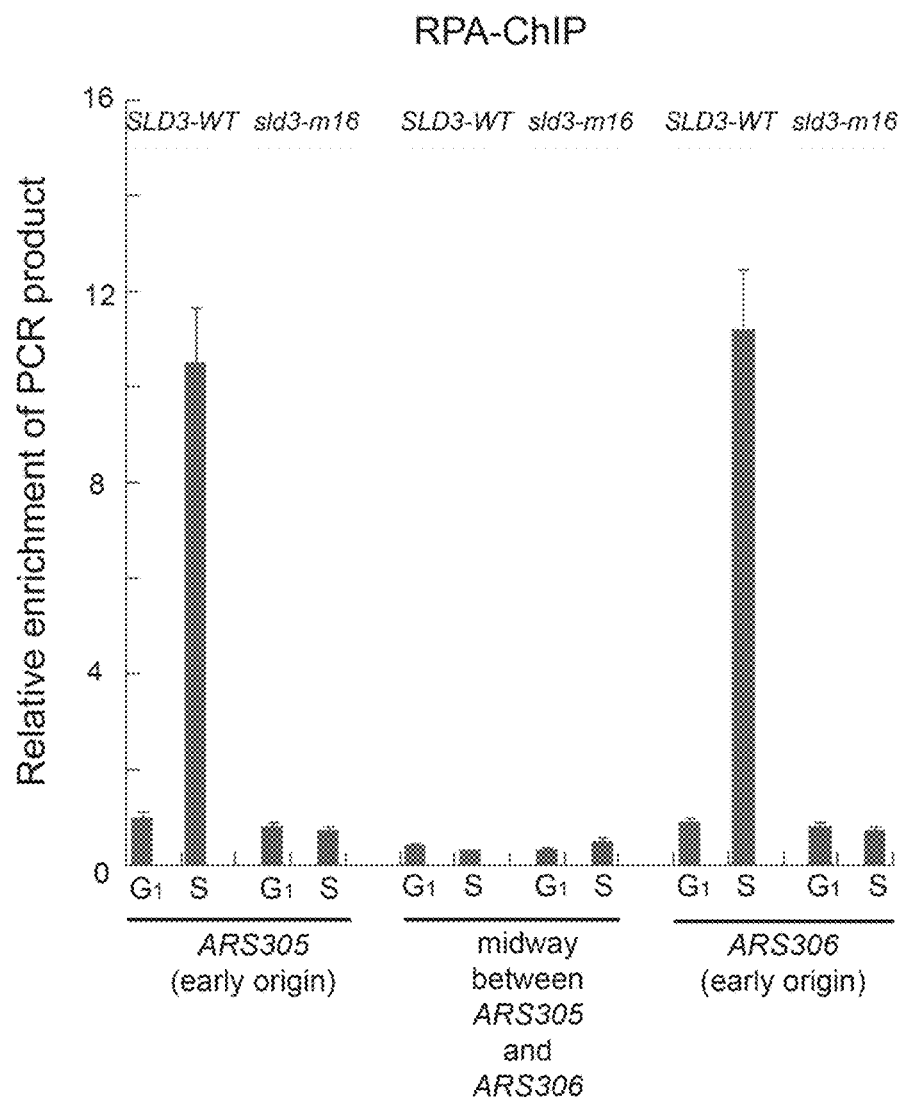
FIG. 9 shows that sld3 stimulation of DDK phosphorylation of Mcm2 is required for RPA-CHiP signal at an origin. Chromatin immunoprecipitation was performed using cells described in FIG. 2A (right panel) at the restrictive temperature, in the presence of galactose, and in a wildtype background. Cells were arrested with α-factor (G1 cells) and then released for 20 minutes (S phase cells). Cells extracts were fixed and immunoprecipitated with antibodies directed against RPA. The immunoprecipate was probed for DNA sequence using quantitative PCR at two early origins (ARS305 or ARS306) and at a region midway between these origins. Results from repeated experiments were quantified and plotted.

It was next determined whether cells expressing sld3-m16 at the restrictive temperature exhibit a defect in RPA-ChIP signal at an origin of replication. For this experiment, cells in $G_1$ were synchronized with α-factor, and then released into medium lacking α-factor for 20 minutes (S phase cells). RPA-ChIP signal at an origin increases in wild-type cells in S phase at the early origins ARS305 and ARS306, coincident with the formation of ssDNA at an origin of replication during S phase (origin melting and replication initiation, FIG. 9). In contrast, cells expressing sld3-m16 do not exhibit an increase in RPA-ChIP signal at an origin of replication as cells are released from α-factor arrest, suggesting that these cells have no origin melting or replication initiation. These results are similar to those observed for expression of mcm2-S164A,S170A (21), suggesting that Sld3-stimulated DDK phosphorylation of Mcm2 is required for origin melting and replication initiation. One possible mechanism for the lack of origin melting for cells expressing sld3-m16 may be that Sld3-stimulation of DDK phosphorylation of Mcm2 is required to disengage Mcm2 from Mcm5 during S phase, allowing for the extrusion of ssDNA from the central channel of Mcm2-7 (21).

Expression of Sld3-m16 Results in Decreased GINS-Mcm2-7 Signal at an Origin of Replication.

Figure 3A:
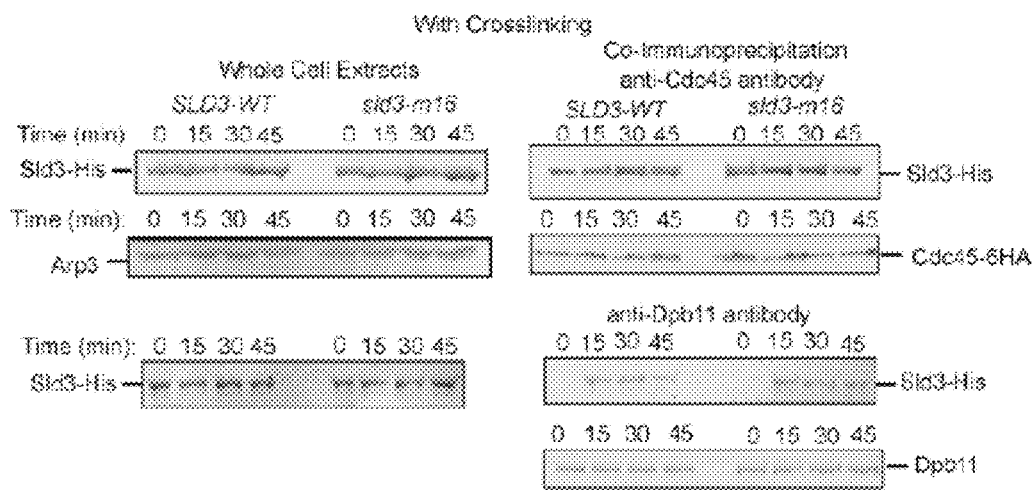
FIG. 3A shows that cells were fixed and analyzed for interaction between Sld3 and Dpb11 or Sld3 and Cdc45. Cells were synchronized in G1 with α-factor and released into medium lacking HU for the indicated times.
Figure 3B:
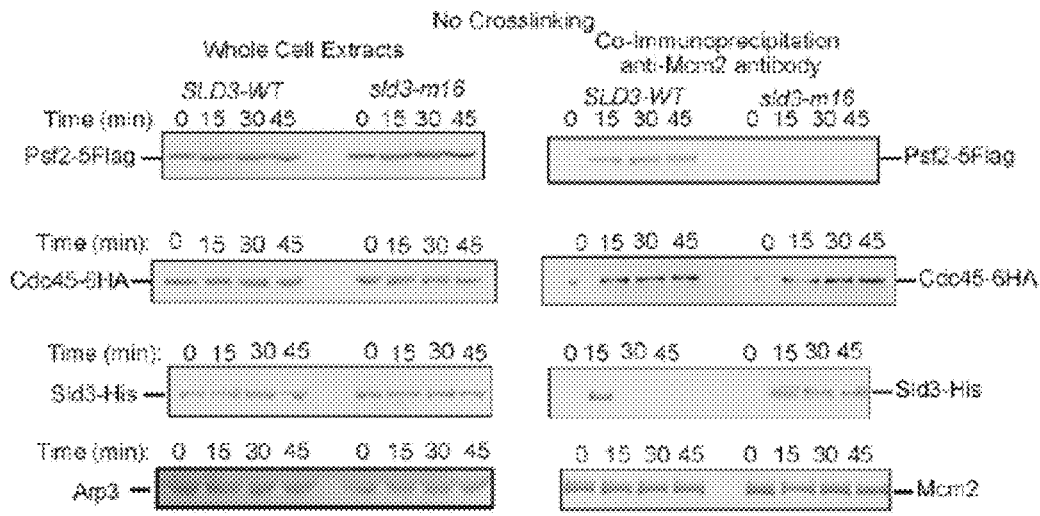
FIG. 3B shows that cells were not fixed and analyzed for interaction between Mcm2-7 and Cdc45, GINS, or Sld3. Overall.

The result of expressing sld3-m16 at the restrictive temperature was next examined on in vivo protein-protein interactions by co-immunoprecipitation analysis (FIGS. 3A and 3B). The effect of Sld3-Cdc45 interaction and Sld3-Dpb11 interaction was first examined using crosslinking, since crosslinking is required to detect these interactions (FIG. 3A). Cells were arrested in $G_1$ with α-factor, and then released into medium lacking α-factor for 0, 15, 30, and 45 minutes. No difference was found in Sld3-Cdc45 interaction (top panels) or Sld3-Dpb11 interaction (bottom panels) with this analysis. These data suggest that expression of sld3-m16 does not affect Sld3-Cdc45 or Sld3-Dpb11 interaction in vivo.

Next, experiments were performed in the absence of crosslinking (FIG. 3B) to observe the interaction between Mcm2-7 and GINS (Psf2, top panels), Mcm2-7 and Cdc45 (middle panels), or Mcm2-7 and Sld3 (bottom panels). No crosslinking is required to observe these interactions. While there is no effect of sld3-m16 on the loading of Cdc45 with Mcm2-7 during S phase (FIG. 3B, middle panels), there is a substantial decrease in GINS interaction with Mcm2-7 in cells expressing sld3-m16 (FIG. 3B, top panels). These data suggest that Sld3-stimulation of DDK phosphorylation of Mcm2 is required for GINS assembly with Mcm2-7. Since there is no origin melting in cells expressing sld3-m16 (FIG. 9), the lack of GINS assembly with Mcm2-7 in mutant cells may reflect that origin melting is required for GINS assembly with Mcm2-7 (15, 16, 26). Sld3-Mcm2-7 interaction was also observed to increase at 30 and 45 minute-time points in mutant cells (FIG. 3B, bottom panels), suggesting that expression of sld3-m16 results in prolonged interaction between Sld3 and Mcm2-7. This observation is consistent with the idea that origin melting is required for Sld3 sequestration from Mcm2-7 (16).

Human Treslin Stimulates Human DDK Phosphorylation of Human Mcm2

DDK phosphorylation of Mcm2 occurs in humans as well as yeast (31), and the human homolog of Sld3 is Treslin (TICRR) (11). A question arose, therefore, as to whether Sld3-stimulation of DDK phosphorylation of Mcm2 was conserved from yeast to humans. Human Mcm2, human DDK, and human Treslin was purified. Human Mcm2 was incubated with human DDK, $\gamma$-$^{32}$P-ATP, and increasing concentrations of Treslin, and the results were analyzed by phosphorimaging and quantitation. Human Treslin was found to stimulate human DDK phosphorylation of human Mcm2 by 15-fold (FIGS. 12A and 12B). Human DDK phosphorylates human Mcm2 at serines 40, 53, and 108 (31). A question then arose as to whether human Treslin stimulates DDK phosphorylation of these residues. Thus, antibodies specific for phophos-40/41, phospho-53, or phospho-108 were obtained (BETHYL Laboratories). Human Treslin was found to substantially stimulate human DDK phosphorylation of human Mcm2 at serines 53 (FIG. 12C, left panel) and 108 (FIG. 12C, middle panel), but not 40/41. These data suggest that Sld3/Treslin stimulation of DDK phosphorylation of Mcm2 is conserved from yeast to human.

Treslin-Stimulation of DDK Phosphorylation of Human Mcm2 May Weaken Mcm2/Mcm5 Interaction.

Figure 12D:
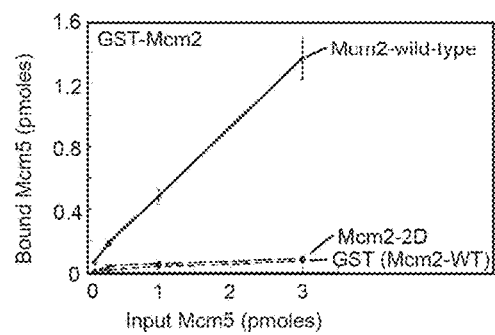
FIG. 12D shows that GST pulldown using 3 pmoles human GST-Mcm2, radiolabeled Mcm5, and 1 mM ATP. Mcm2-2D is Mcm2-S53D,S108D.
Figure 12E:
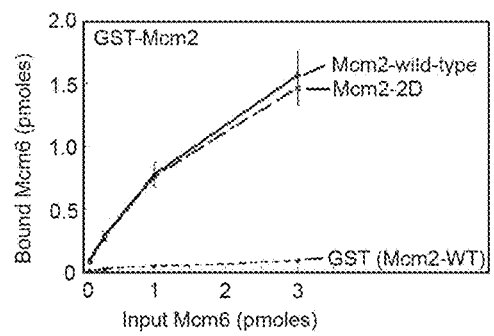
FIG. 12E is similar to FIG. 12D, except radiolabeled Mcm6 was used as the input protein.
Figure 12F:
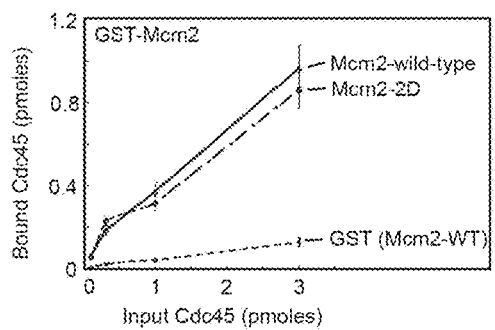
FIG. 12F is similar to FIG. 12D, except radiolabeled Cdc45 was used as the input protein. Overall.

It was also found previously that a mutant of yeast Mcm2 that mimics DDK phosphorylation (Mcm2-5164D,S170D) exhibits substantially diminished interaction with Mcm5 compared to wild-type Mcm2 (21). The Mcm2-Mcm5 interaction functions as a 'gate' to allow the Mcm2-7 complex to encircle single or double-stranded DNA (22). To determine if DDK-phosphorylation of Mcm2 inhibits the interaction with Mcm5 in humans, human GST-Mcm2 was incubated with radiolabeled Mcm5 in the presence of ATP (FIG. 12D). While wild-type Mcm2 bound tightly to Mcm5, the DDK-phosphomimic form of human Mcm2 (Mcm2-2D or Mcm2-S53D,S108D) exhibited substantially diminished interaction with Mcm5. Furthermore, Mcm2-2D bound to human Mcm6 (FIG. 12E) and human Cdc45 (FIG. 12F) like wild-type Mcm2, suggesting that the loss of interaction of Mcm2 with Mcm5 is specific. These data also suggest that Sld3/Treslin-stimulation of DDK phosphorylation of Mcm2 reduces the interaction between Mcm2 and Mcm5 in a manner that is conserved from yeast to humans, and thus a potential regulatory mechanism may be conserved to open the Mcm2-7 'gate' during S phase. This mechanism may function along with other factors to allow for the extrusion of ssDNA from the central channel of Mcm2-7 during S phase (origin melting).

Expression of Sld3-m16 Yields Similar Phenotype as Expression of Mcm2-S164A,S170A.

Figure 10:
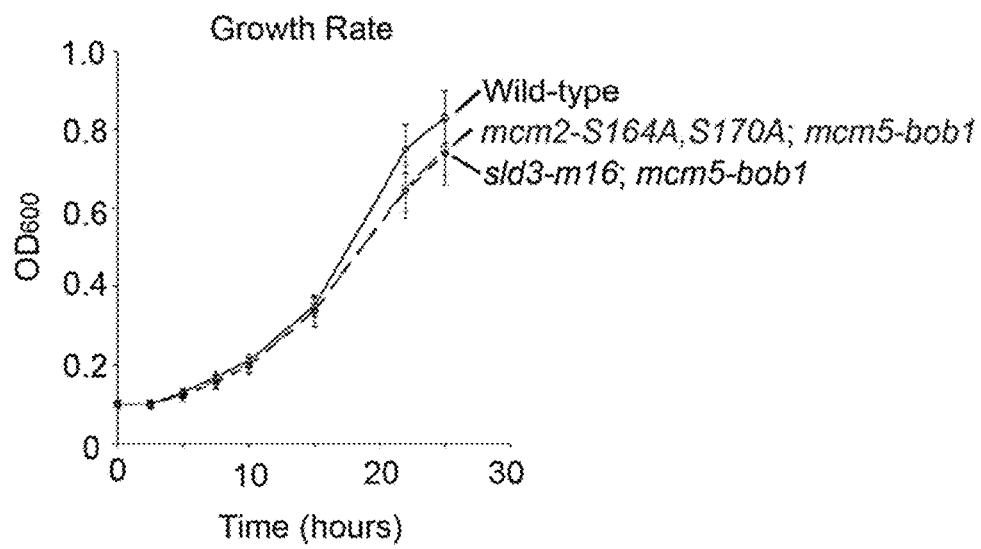
FIG. 10 shows that the growth rate of sld3-m16; mcm5-bob1 and mcm2-S164A,S170A; mcm5-bob1 are very similar. The growth of the indicated strains in liquid media were determined and plotted as a function of time.
Figure 11:
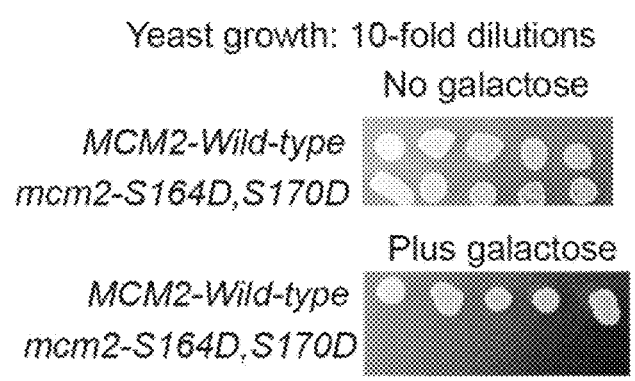
FIG. 11 shows that expression of mcm2-S164D,S170D is lethal. 10-fold dilution of budding yeast cells harboring a plasmid with galactose-induced expression of mcm2-S164D,S170D. In the presence of galactose, with induced expression of mcm2-S164D,S170D, cells are dead on agar plates.

The data seen herein, compared to that of previous work from the current inventors (21), indicate that expression of sld3-m16 yields similar phenotype as expression of mcm2-S164A,S170A. Expression of either mutation yields no growth on agar plates, and is suppressed by mcm5-bob1. Furthermore, FACS analysis of S phase progression, RPA-ChIP analysis, and Co-IP analysis yield very similar results. To further compare the phenotypes of these two mutants, the growth rate in solution of sld3-m16; mcm5-bob1 cells was analyzed and compared to mcm2-S164A,S170A; mcm5-bob1 cells (FIG. 10). The growth rates of these two strains are very similar, suggesting that the phenotypes of these two mutations are indeed very similar. These data lend further support to the idea that the primary defect in sld3-m16 cells is a lack of DDK phosphorylation of Mcm2. The current inventors thus sought to test whether expression of mcm2-S164D,S170D can suppress the growth defect conferred by expression of sld3-m16, but unfortunately cells expressing mcm2-S164D,S170D cells are dead on agar plates (FIG. 11). These data suggest that the unphosphorylated state of Mcm2 may be required for cell growth.

Discussion of Examples

DDK Phosphorylation of Mcm2 is Coordinated with Cdc45 Recruitment to Mcm2-7

The yeast strain harboring genomic mcm2-S164A,S170A under control by native promoter (27, 28) was found to exhibit normal growth upon galactose-induced overexpression of mcm2-S164A,S170A (FIG. 7B). These data suggest that this native-promoter strain harbors a suppressor mutation, and the data further support that DDK phosphorylation of Mcm2 is required for growth under normal growth conditions. It was also found with co-immunoprecipitation analysis that DDK-phosphorylated Mcm2 is enriched for Cdc45 interaction in vivo compared to Mcm2 (FIG. 1A), suggesting that Mcm2-7 complexes that bind to Cdc45 are also phosphorylated by DDK. These data suggest that some mechanism exists to coordinate DDK phosphorylation of Mcm2 with Cdc45 recruitment to Mcm2-7.

Sld3 Stimulates DDK Phosphorylation of Mcm2.

Yeast Sld3 was found to stimulate yeast DDK phosphorylation of yeast Mcm2 by 11-fold using purified proteins (FIGS. 1B and 1C). Phosphorylation of serine 164 and serine 170 of yeast Mcm2 was found to be substantially enhanced by the addition of Sld3 to DDK (FIG. 1D). This stimulation also occurs when Mcm2-7 is present as a hexameric complex (FIG. 1E). The C-terminal region of Sld3 was found to be responsible for the stimulation of DDK phosphorylation of Mcm2, and after extensive screening of the C-terminal region a mutant of Sld3, Sld3-m16 (Sld3-S556A,H557A,S558A,T559A), was identified and is specifically defective in stimulating DDK phosphorylation of Mcm2 (FIGS. 6A-6E).

Sld3 Stimulation of DDK Phosphorylation of Mcm2 May be Important for Origin Melting and GINS Assembly with Mcm2-7.

Expression of sld3-m16 confers a dominant negative severe growth defect in budding yeast cells that is suppressed by mcm5-bob1 (FIG. 2A). Expression of wild-type levels of sld3-m16 also results in a severe growth and DNA replication defect (FIGS. 2A, 2B, and 2D). DDK phosphorylation of Mcm2 is undetectable in cells expressing sld3-m16 compared to wild-type cells (FIG. 2C), suggesting that Sld3 substantially stimulates DDK phosphorylation of Mcm2 in vivo. Cells expressing sld3-m16 exhibit a substantially reduced RPA-ChIP signal in S phase (FIG. 9), suggesting that Sld3 stimulation of DDK phosphorylation of Mcm2 is important for origin melting and subsequent replication initiation. Co-immunoprecipitation analysis supports that Sld3-stimulation of DDK phosphorylation of Mcm2 is important for GINS association with Mcm2-7 and also timely disengagement of Sld3 from Mcm2-7 (FIG. 3). These results are consistent with previous data suggesting that DDK phosphorylation of Mcm2 is required for origin melting and subsequent sequestration of Sld3 from Mcm2-7, allowing the assembly of GINS with Mcm2-7 (21). Furthermore, the phenotypes of cells expressing sld3-m16 and mcm2-S164A,S170A are very similar, suggesting that the primary defect in cells expressing sld3-m16 is the lack of DDK phosphorylation of Mcm2.

Human Treslin Stimulates DDK Phosphorylation of Mcm2.

Human Treslin was found to stimulate human DDK phosphorylation of human Mcm2 by 15-fold (FIGS. 12A and 12B), and serines 53 and 108 were found to be phosphorylated in response to Treslin stimulation of DDK phosphorylation of Mcm2 (FIGS. 12C and 12D). Furthermore, the phosphomimic form of human Mcm2 (Mcm2-2D or Mcm2-S53D,S108D), binds substantially weaker to Mcm5 compared to unmodified Mcm2, suggesting a potential mechanism for Mcm2-7 'gate' opening with subsequent origin melting.

A Conserved Mechanism to Couple Helicase Assembly with Helicase Phosphorylation is Presented Herein.

A large excess of Mcm2-7 complexes are loaded onto dsDNA relative to the number of Mcm2-7 complexes that actually fire during replication initiation (29). Furthermore, Sld3 and DDK are two limiting factors for DNA replication, along with Sld2 and Dpb11 (32). Thus, a question arises as to the mechanism that orchestrates the set of events that are required for origin firing at an activated Mcm2-7 double hexamer. It is shown herein that Sld3 may be critical for this orchestration, since Sld3 may couple recruiting Cdc45 to Mcm2-7 with stimulation of DDK phosphorylation of Mcm2. It is important to emphasize that DDK phosphorylation of Mcm2 does not cause the Cdc45 recruitment to Mcm2-7. Instead, DDK phosphorylation of Mcm2 is correlated with Cdc45 recruitment to Mcm2-7. This correlation is the results of Sld3 binding to Mcm2-7. When Sld3 binds to Mcm2-7, Sld3 simultaneously recruits Cdc45 to Mcm2-7, and Sld3 stimulates DDK phosphorylation of Mcm2.

A Model for Replication Initiation is Presented Herein.

Figure 4:
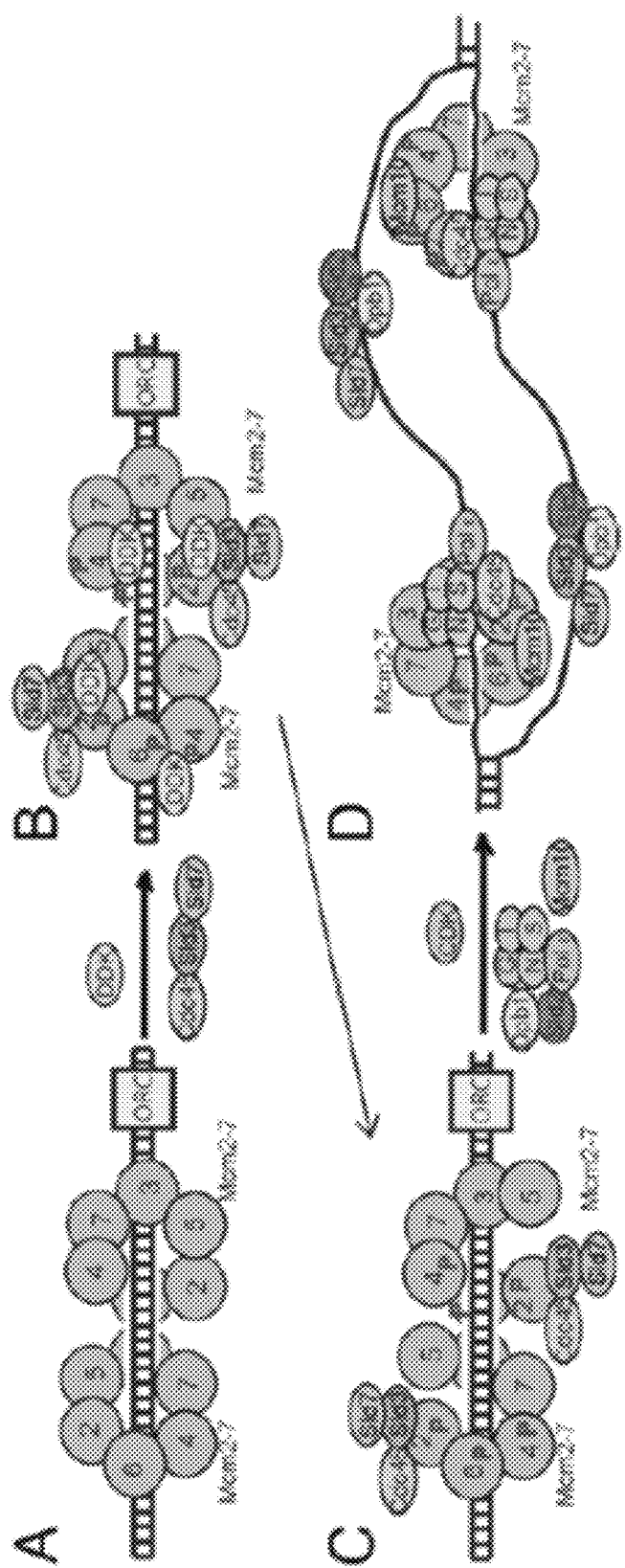
FIG. 4 depicts a model for the initiation of DNA replication. Panel A shows that Mcm2-7 loads as double hexamer to encircle dsDNA during late M and $G_1$ phases. Panel B shows that in S phase, Sld3, along with Sld7, recruits Cdc45 to Mcm2-7. Sld3, while bound to Mcm2-7, substantially stimulates DDK phosphorylation of Mcm2. DDK also phosphorylates Mcm4 and Mcm6. Sld3 also blocks the premature interaction between GINS and Mcm2-7. Panel C shows that once Mcm2 is phosphorylated by DDK, the interaction between Mcm2 and Mcm5 weakens, allowing single-strand extrusion from the central channel of Mcm2-7 (origin melting). Panel D shows that Sld3-Sld2-Dpb11 form a CDK-dependent ternary complex in S phase. Once the origin is melted, Sld3-Sld2-Dpb11 is released from Mcm2-7, since Sld3-Sld2-Dpb11 binds preferentially to ssDNA. The sequestration of Sld3-Sld2-Dpb11 onto ssDNA allows GINS to engage with Cdc45-Mcm2-7, and the CMG helicase is assembled and activated for unwinding.

A model for the initiation of DNA replication is shown in FIG. 4. In late M and the origin recognition complex (Orc), along with Cdc6 and Cdt1, promote the loading of Mcm2-7 as a double hexamer to surround dsDNA (FIG. 4, panel A) (6, 7, 33, 34). In S phase, Sld3-Sld7 recruits Cdc45 to Mcm2-7 (2, 17, 24, 35) (FIG. 4, panel B). Sld3, once bound to Mcm2-7, substantially stimulates DDK phosphorylation of Mcm2. Sld3 also blocks the premature interaction between GINS and Mcm2-7 (16, 23). DDK also phosphorylates Mcm4 and Mcm6 (18, 19, 36-38). The Mcm2-7 double hexamer then dissociates to single hexamers by an unknown mechanism (39). Once DDK phosphorylates Mcm2, and possibly with the aid of accessory proteins, Mcm2 loses its affinity for Mcm5 (FIG. 4, panel C) (21). This allows for single-strand extrusion from the central channel of Mcm2-7 (i.e., origin melting). Origin melting generates ssDNA that sequesters the Sld3-Sld2-Dpb11 complex onto ssDNA, removing Sld3-Sld2-Dpb11 from Mcm2-7 (15, 16, 26). This sequestration allows GINS to bind Cdc45-Mcm2-7 (FIG. 4, panel D). The CMG replication fork helicase is now fully assembled and activated.

Example 2

Figure 6:
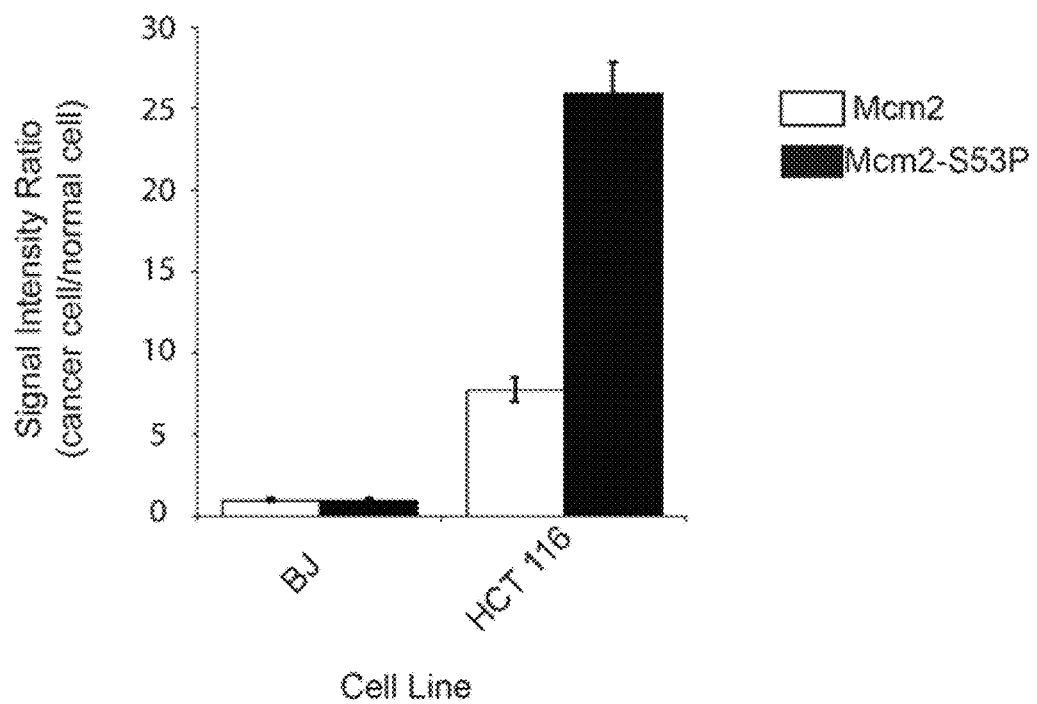
FIG. 6 shows that human colorectal cancer cell line expresses higher levels of Mcm2-S53P compared to normal cells. Cell extracts from a normal human cell line (BJ human foreskin fibroblasts), or a colorectal cancer cell line (HCT 116) were analyzed by Western analysis and probed for Mcm2-S53P or Mcm2. PonceauS staining revealed equivalent levels of protein transfer for each lane. The bands were quantified and plotted as a function of signal intensity ratio (cancer cell/normal cell) for Mcm2-S53P or for Mcm2. The experiments were repeated in triplicate and the mean±SEM is shown.

HCT116 colorectal cancer and normal cells was tested for the expression of Mcm2 and DDK-phosphorylated Mcm2 (Mcm2-S53P) (FIG. 6). The current antibody that recognizes DDK-phosphorylated Mcm2 was found to produce a clear signal by Western analysis of whole cell extracts. Furthermore, a higher signal for Mcm2-S53P was found in colorectal cancer cells compared to normal cells (FIG. 6). These data suggest that this antibody is useful to detect cancer. Levels of Mcm2 were also examined, and it was found that while cancer cells expressed higher levels of Mcm2 compared to normal cells, the signal ratio (cancer cells/normal cells) was substantially higher for Mcm2-S53P compared to Mcm2 (FIG. 6). These data suggest that Mcm2-S53P can predict cancer with higher specificity compared to Mcm2, and Mcm2 is already a proven standard in the field.

Glossary of Claim Terms

Administer: This term is used herein to refer to the process by which purified Treslin or a composition comprising Treslin as an active agent, is delivered to elevate phosphorylation capacity of Mcm. Administration will often depend upon the amount of compound administered, the number of doses, and duration of administration. In an embodiment, multiple doses of the agent are administered. The frequency of administration of the agent can vary depending on any of a variety of factors, such as extent of high blood glucose levels, and the like. The duration of administration of the agent, e.g., the period of time over which the agent is administered, can vary, depending on any of a variety of factors, including response, etc. Optimization of such factors is well within the level of skill in the art, unless otherwise noted.

Clinically effective amount: This term is used herein to refer to concentrations or amounts of components such as agents (e.g., purified Treslin) which are effective for producing an intended result, including elevating phosphorylation capacity of Mcm.

Detect: This term is used herein to refer to identifying the presence of a particular moiety (e.g., phosphorylated Mcm), the levels thereof, and or the interactions thereof with other moieties (e.g., antibody).

Elevated levels of phosphorylated Mcm: This term is used herein to refer to a degree or amount of phosphorylated Mcm that is higher than the degree or amount of phosphorylated Mcm found naturally in a healthy or otherwise non-cancerous human being.

Modulate: This term is used herein to refer to regulating or otherwise using a moiety (e.g., DDK) to effectuate a desired result (e.g., phosphorylation of Mcm).

Normal levels of phosphorylated Mcm: This term is used herein to refer to a degree or amount of phosphorylated Mcm that is found naturally in a healthy or otherwise non-cancerous human being.

Patient: This term is used herein to refer to humans and mammals (e.g., primates, mice, rats, pigs, cats, dogs, and horses). For diagnostic or research applications, a wide variety of mammals will be suitable subjects, including rodents (e.g., mice, rats, hamsters), rabbits, primates, and swine such as inbred pigs and the like.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A method of detecting elevated levels of phosphorylated minichromosome maintenance protein complex (Mcm) in a patient, comprising:
   obtaining a sample from a human patient; and
   modulating Dbf4-Cdc7 kinase (DDK) to facilitate phosphorylation of said Mcm, said modulation is performed by using Treslin to stimulate phosphorylation of said Mcm by said DDK;
   detecting whether said phosphorylated Mcm is elevated in said sample relative to normal levels, by contacting said sample with an anti-Mcm antibody and detecting binding between said phosphorylated Mcm and said antibody.

2. A method as in claim 1, wherein at least one of a plurality of phosphorylation-stimulating fragments of Treslin is used, said phosphorylation-stimulating fragments being amino acids 833-1133, amino acids 833-1267, amino acids 833-1910, amino acids 833-1000, amino acids 1000-1267, and amino acids 1000-1133 of SEQ ID NO:1.

3. A method as in claim 1, wherein said phosphorylated Mcm is human Mcm present at serine 53.

4. A method as in claim 1, wherein said phosphorylated Mcm is human Mcm present at serine 108.

5. A method as in claim 1, wherein said phosphorylated Mcm is phosphorylated Mcm2.

6. A method as in claim 5, wherein said phosphorylated Mcm2 is human Mcm2 at serine 53 or serine 108.

7. A method as in claim 1, wherein said sample is a tissue sample.

8. A method for increasing capacity for phosphorylation of Mcm in a biological sample, comprising administering a clinically effective amount of purified Treslin to said biological sample to increase phosphorylation of said Mcm by DDK, whereby said DDK is recruited to said Mcm to bridge said DDK and said Mcm together in an active state.

9. A method as in claim 8, wherein at least one of a plurality of phosphorylation-stimulating fragments of Treslin is used, said phosphorylation-stimulating fragments being amino acids 833-1133, amino acids 833-1267, amino acids 833-1910, amino acids 833-1000, amino acids 1000-1267, and amino acids 1000-1133 of SEQ ID NO:1.

10. A method as in claim 8, wherein said Mcm is Mcm2.

11. A method as in claim 10, wherein said Mcm2 is human Mcm2 phosphorylated at serine 53 or serine 108.

12. A method as in claim 8, wherein said clinically effective amount is about 3 pmoles of Treslin.

13. A method of diagnosing colorectal cancer in a patient, comprising:
  obtaining a sample from a human patient;
  modulating Dbf4-Cdc7 kinase (DDK) to facilitate phosphorylation of Mcm, said modulation is performed by using Treslin to stimulate phosphorylation of said Mcm by said DDK;
  detecting whether said phosphorylated Mcm is elevated in said sample relative to normal levels, by contacting said sample with an anti-Mcm antibody and detecting binding between said phosphorylated Mcm and said antibody; and
  diagnosing said patient with cancer when an elevated level of said phosphorylated Mcm is detected.

14. A method as in claim 13, wherein said phosphorylated Mcm is phosphorylated Mcm2.

15. A method as in claim 14, wherein said phosphorylated Mcm2 is human Mcm 2 at serine 53 or serine 108.

16. A method as in claim 8, wherein said sample is a tissue sample.

\* \* \* \* \*